(12) United States Patent
Doctor et al.

(10) Patent No.: US 8,962,340 B2
(45) Date of Patent: Feb. 24, 2015

(54) REAL-TIME ASSAY FOR THE DETECTION OF BOTULINUM TOXIN

(71) Applicant: SRC, Inc., North Syracuse, NY (US)

(72) Inventors: Kenton Arthur Doctor, East Syracuse, NY (US); Stacey Ann Massulik, Syracuse, NY (US); Frances Louise Stites, Ashburn, VA (US); Timothy Francis Moshier, Volney, NY (US); Jeffrey Harold Mills, Liverpool, NY (US); Lisa Helen Chamberlin, East Syracuse, NY (US); Deborah L. Plochocki, Marcellus, NY (US); Olivia Jennifer Barrett, Cicero, NY (US); Huda Sirageldin Suliman, North Syracuse, NY (US)

(73) Assignee: SRC, Inc., North Syracuse, NY (US)

( * ) Notice: Subject to any disclaimer, the term of this patent is extended or adjusted under 35 U.S.C. 154(b) by 0 days.

(21) Appl. No.: 13/839,827

(22) Filed: Mar. 15, 2013

(65) Prior Publication Data

US 2014/0154812 A1 Jun. 5, 2014

Related U.S. Application Data

(60) Provisional application No. 61/732,436, filed on Dec. 3, 2012.

(51) Int. Cl.
*C07K 7/00* (2006.01)
*G01N 21/62* (2006.01)
*G01N 33/569* (2006.01)

(52) U.S. Cl.
CPC ............ *C07K 7/00* (2013.01); *G01N 33/56911* (2013.01); *G01N 2333/33* (2013.01)
USPC ........... 436/86; 422/82.08; 530/324; 435/6.1; 435/283.1

(58) Field of Classification Search
None
See application file for complete search history.

(56) References Cited

U.S. PATENT DOCUMENTS

| | | | |
|---|---|---|---|
| 6,504,006 B1 | 1/2003 | Shine et al. | |
| 7,598,027 B2 | 10/2009 | Fernandez-Salas et al. | |
| 7,645,570 B2 | 1/2010 | Fernandez-Salas et al. | |
| 7,674,601 B2 | 3/2010 | Williams et al. | |
| 7,838,260 B2 | 11/2010 | Steward et al. | |
| 8,022,172 B2 | 9/2011 | Williams et al. | |
| 8,048,643 B2 | 11/2011 | Steward et al. | |
| 8,053,209 B2 | 11/2011 | Steward et al. | |
| 8,124,357 B2 | 2/2012 | Fernandez-Salas et al. | |
| 8,137,924 B2 | 3/2012 | Chapman et al. | |
| 8,138,909 B2 | 3/2012 | Lewington et al. | |
| 8,257,914 B2 | 9/2012 | Fernandez-Salas et al. | |
| 2006/0134722 A1* | 6/2006 | Chapman et al. | 435/23 |
| 2007/0243565 A1* | 10/2007 | Williams et al. | 435/7.32 |
| 2007/0292844 A1 | 12/2007 | Tilles et al. | |
| 2008/0032318 A1* | 2/2008 | Steward et al. | 435/7.32 |
| 2009/0176259 A1* | 7/2009 | Kalkum et al. | 435/7.94 |
| 2012/0088680 A1 | 4/2012 | Robinson et al. | |
| 2012/0202754 A1 | 8/2012 | Schmidt et al. | |

FOREIGN PATENT DOCUMENTS

| | | |
|---|---|---|
| JP | 2002176982 | 6/2002 |
| WO | 2011003941 | 1/2011 |

OTHER PUBLICATIONS

Schmidt et al. (Fluorigenic Substrates for the Protease Activities of Botulinum Neurotoxins, Serotypes A, B, and F, Applied and Environmental Microbiology, Jan. 2003, p. 297-303).*

Ruge et al. (Detection of six serotypes of botulinum neurotoxin using fluorogenic reporters, Analytical Biochemistry 411 (1/12011) 200-209).*

Capek et al. "Sensing the deadliest toxin: Technologies for botulinum neurotoxin detection" Toxins, 2010, 2, pp. 24-53.

Morse, Ed. Bioterrorism; InTech: Published Online, 2012. Cheng et al. "Current methods for detecting the presence of botulinum neurotoxins in food and other biological samples", pp. 1-16.

Scarlatos et al. "Methods for detecting botulinum toxin with applicability to screening foods against biological terrorist attacks" Journal of Food Science, 2005, 70, pp. r121-r130.

* cited by examiner

*Primary Examiner* — Stephanie K Mummert
*Assistant Examiner* — Aaron Priest
(74) *Attorney, Agent, or Firm* — George R. McGuire; David L. Nocilly; Bond Schoeneck & King, PLLC

(57) ABSTRACT

A real-time portable and rapid detection assay to identify the presence of biologically active toxins such as botulinum toxins. The proteolytic activity of BoNT/A is measured using a peptide cleavage assay, where a fluorescent substrate is cleaved by BoNT/A, resulting in increased fluorescence. This fluorescence can be monitored in real-time using a fluorescence detection instrument, such as a real-time PCR system that has been modified to implement a detection algorithm specific to the identification of the target toxin.

7 Claims, 47 Drawing Sheets

FIGURE 1

Sequence 1

ExPASy cleavage predictions for the fluor/quencher region:

```
              Ch 1o LysN ProtK
        CNBr Ch 1o Pn1.3 Pn2 Therm
              LysC Therm Tryps
                    LysN ProtK
                         ProtK
        ArgC Clost Therm Tryps
                    ProtK
              Glu ProtK Staph
              AspGluN HCOOH
         AspN AspGluN ProtK
    ArgC Clost Therm Tryps
              ProtK Sequence 3

ExPASy cleavage predictions for the fluor/quencher region:

```
                           Ch lo LysN ProtK
              CNBr Ch lo Pn1.3 Pn2 Therm
                    LysC Therm Tryps
                         LysN ProtK
                         ProtK Therm
                    ArgC Clost Tryps
                                ProtK
                                Therm
                                ProtK
                                HCOOH
AspN AspGluN Glu ProtK Staph
    ArgC AspGluN Clost Tryps
                         ProtK
                    LysC Tryps
                                        KTREDIQNATARKMLK
              1                    +              16
```

Protease cleavage sites in the fluor/quencher region of SEQ. ID NO. 3
(Arginine site still in correct location for BoNT/A mediated cleavage)

Sequence 4

ExPASy cleavage predictions for the fluor/quencher region:

```
         Ch lo LysN ProtK
              CNBr Ch lo Therm
              LysC Therm Tryps
         ArgC Clost LysN Tryps
                         ProtK
                    ProtK Therm
                         ProtK
                         Therm
                         ProtK
                         HCOOH
AspN AspGluN Glu ProtK Staph
    ArgC AspGluN Clost Tryps
                         ProtK
                    LysC Tryps
                                        KTREDIQNATARKMLK
              1                    +              16
```

Protease cleavage sites in the fluor/quencher region of SEQ. ID NO. 4
(Pepsin does not cleave this substrate)

FIGURE 12B $n$ = Number of Cycles Completed $c$ = Negative Control Fluorescence $\mu$ = Negative Control Fluorescence Mean $m_c$ = Negative Control Slope $\overline{m_c}$ = Negative Control Slope Mean $\sigma_c$ = Negative Control Standard Deviation $\sigma\, m_c$ = Negative Control Slope Standard Deviation $X$ = Assay Fluorescence $\bar{x}$ = Assay Fluorescence Mean $m_x$ = Assay Slope $\overline{m_x}$ = Assay Slope Mean $F$ = Fluorescence sub-score $S$ = Slope sub-score $w_F$ = Weight of Fluorescence sub-score $w_S$ = Weight of Slope sub-score $$\mu = \frac{1}{n}\sum_{i=0}^{n} c_i$$

$$m_c = \frac{c_i - c_{i-1}}{n - (n-1)} = \frac{c_i - c_{i-1}}{1} = c_i - c_{i-1}$$

$$\overline{m_c} = \frac{1}{n}\sum_{i=0}^{n}(c_i - c_{i-1})$$

$$\sigma_c = \sqrt{\sum_{i=0}^{n}(C_i - m)^2}$$

$$\sigma\, m_c = \sqrt{\sum_{i=0}^{n}(C_i - m)^2}$$

$$\bar{x} = \frac{1}{n}\sum_{i=0}^{n} x_i$$

$$m_x = \frac{x_i - x_{i-1}}{i - (i-1)} = \frac{x_i - x_{i-1}}{1} = x_i - x_{i-1}$$

$$\overline{m_x} = \frac{1}{n}\sum_{i=0}^{n}(x_i - x_{i-1})$$

FIGURE 24

REAL-TIME ASSAY FOR THE DETECTION OF BOTULINUM TOXIN

CROSS-REFERENCE TO RELATED APPLICATIONS

The present application claims priority to U.S. Provisional Application No. 61/732,436, filed on Dec. 3, 2012.

BACKGROUND OF THE INVENTION

1. Field of the Invention

The present invention relates to the detection of biologically active botulinum toxins and, more specifically, to a real-time assay for detecting biologically active botulinum toxins that can be implemented in the field.

2. Description of the Related Art

Botulinum neurotoxins (BoNTs) are proteins produced by the bacteria *Clostridium botulinum*. BoNTs are powerful toxins that cause the life threatening illness, botulism, in humans, with BoNT serotype A (BoNT/A) being one of the most potent. BoNTs produce their toxic effects by entering neurons and then cleaving N-ethylmaleimide-sensitive factor activating protein receptor (SNARE) proteins. In particular, BoNT/A specifically cleaves SNAP-25 which prevents the formation of a synaptic fusion complex and thereby inhibits the release of acetylcholine, resulting in muscle fiber paralysis. BoNT exposure is fatal without immediate diagnosis and proper treatment. Due to their ease of production, BoNTs pose a major biological warfare threat.

Early detection of BoNTs is crucial for bio-security and food safety. Real-time quantitative polymerase chain reaction (qPCR) is a very common detection method used in the biodefense field. qPCR is a very sensitive and quick method for detecting biological organisms by amplifying specific regions of deoxyribonucleic acid (DNA), and can be used to detect the genes coding for BoNTs. However, BoNTs are proteins that do not require the intact organism to cause disease, and can be purified from the organism. The purified toxin, which consists of 100-kDa heavy chain (HC; required for cell entry) joined by a disulfide bond to a 50-kDa light chain (LC; required for SNAP-25 cleavage), may be completely devoid of DNA and therefore not detectable using qPCR. qPCR has the ability to detect the gene coding for a protein toxin, but it does not directly detect the presence, or more importantly the activity of protein toxins.

BRIEF SUMMARY OF THE INVENTION

It is therefore a principal object and advantage of the present invention to provide a real-time assay for the detection of biologically active botulinum toxins.

In accordance with the foregoing objects and advantages, the present invention provides a real-time portable and rapid detection assay to identify the presence of biologically active toxin such as botulinum toxins. The detection assay includes a BoNT/A sensing fluorescent substrate, a negative control/interferent sensing fluorescent substrate, a qPCR detection protocol modified for toxin identification, and a toxin detection algorithm. The proteolytic activity of BoNT/A can be measured using a peptide cleavage assay, where a synthesized dual labeled fluorescent peptide substrate is cleaved by BoNT/A, resulting in increased fluorescence based on Forester (fluorescence) resonance energy transfer (FRET) principles.

While assays according to the present invention may use a commercially available fluorescent peptide substrate that mimics the BoNT/A cleavage site of SNAP-25 (such as SNAPtide® peptide available from List Biological Laboratories), the detection assay may be made more stable and more sensitive by using a fluorescent peptide substrate (SEQ. ID NO. 1) that mimics both the BoNT/A binding and cleavage sites of SNAP-25. Additionally, a negative control/interferent sensing fluorescent peptide substrate (SEQ. ID NO. 2) was designed based on SEQ. ID NO. 1 so that it would be cleaved or inhibited by the same proteases or inhibitors that would affect SEQ. ID NO. 1, but at the same time be insensitive to BoNT/A proteolytic activity due to a mutated BoNT/A cleavage site.

The increase in fluorescence in SEQ. ID NO. 1 caused by BoNT/A activity can be monitored in real-time using any temperature controlled fluorimeter (e.g. the FilterMax® F5 Multimode Microplate Reader available from Molecular Devices), any lab-based qPCR fluorescence detection instrument (e.g. the Rotor-Gene® Q available from Qiagen) running a qPCR detection protocol modified for toxin identification, or any field-based qPCR fluorescence detection instrument (e.g. the RAZOR® EX available from BioFire Diagnostics or the Genedrive® available from Epistem) running a qPCR detection protocol modified for toxin identification. The ruggedized RAZOR® EX and the small form factor Genedrive® are portable qPCR based platforms designed for use outside of a laboratory environment that have the ability to detect fluorescence changes in less than 1 hour for biodefense (RAZOR® EX) and point of care diagnostics (Genedrive®). Fluorescence data generated in the fluorescence detection instruments is then applied to a toxin detection algorithm, which utilizes data from a sample exposed to both SEQ. ID NO. 1 and SEQ. ID NO. 2 to determine if biologically active BoNT/A toxin is present or absent in the test sample. qPCR platforms are preferred over basic temperature controlled fluorimeters because they allow the operator to use a single instrument to screen one sample using conventional qPCR for genetic detection of biological threat agents (such as the *Bacillus anthracis* and *Francisella tularensis* qPCR assays) and non-conventional activity screening for biological activity detection of toxins (such as the BoNT/A activity assay describe here).

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of an assay for detecting botulinum toxin according to the present invention using the proof-of-principle fluorescent peptide SNAPtide® or the designed fluorescence peptide SEQ. ID NO. 1.

Figure 3A:
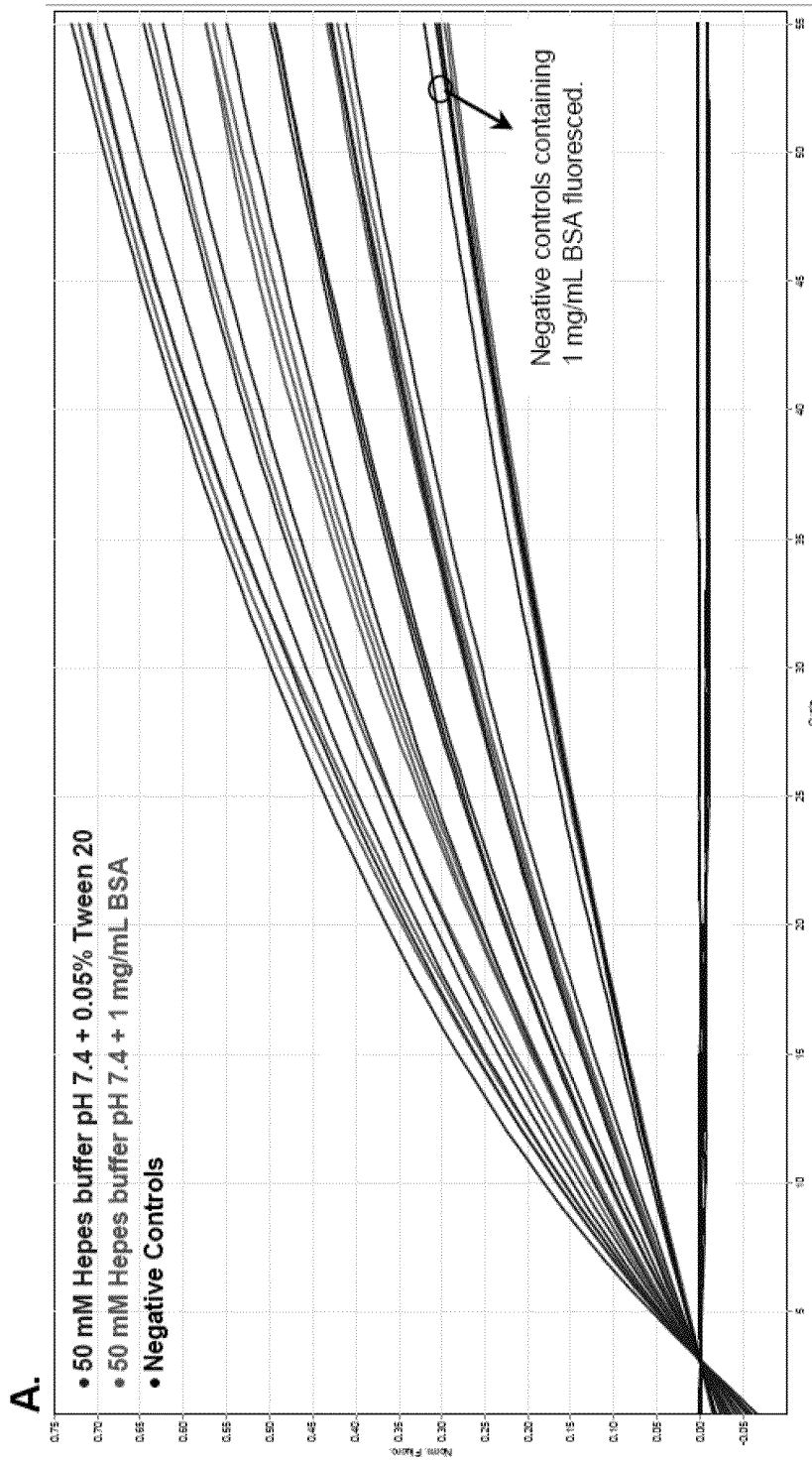
Figure 3B:
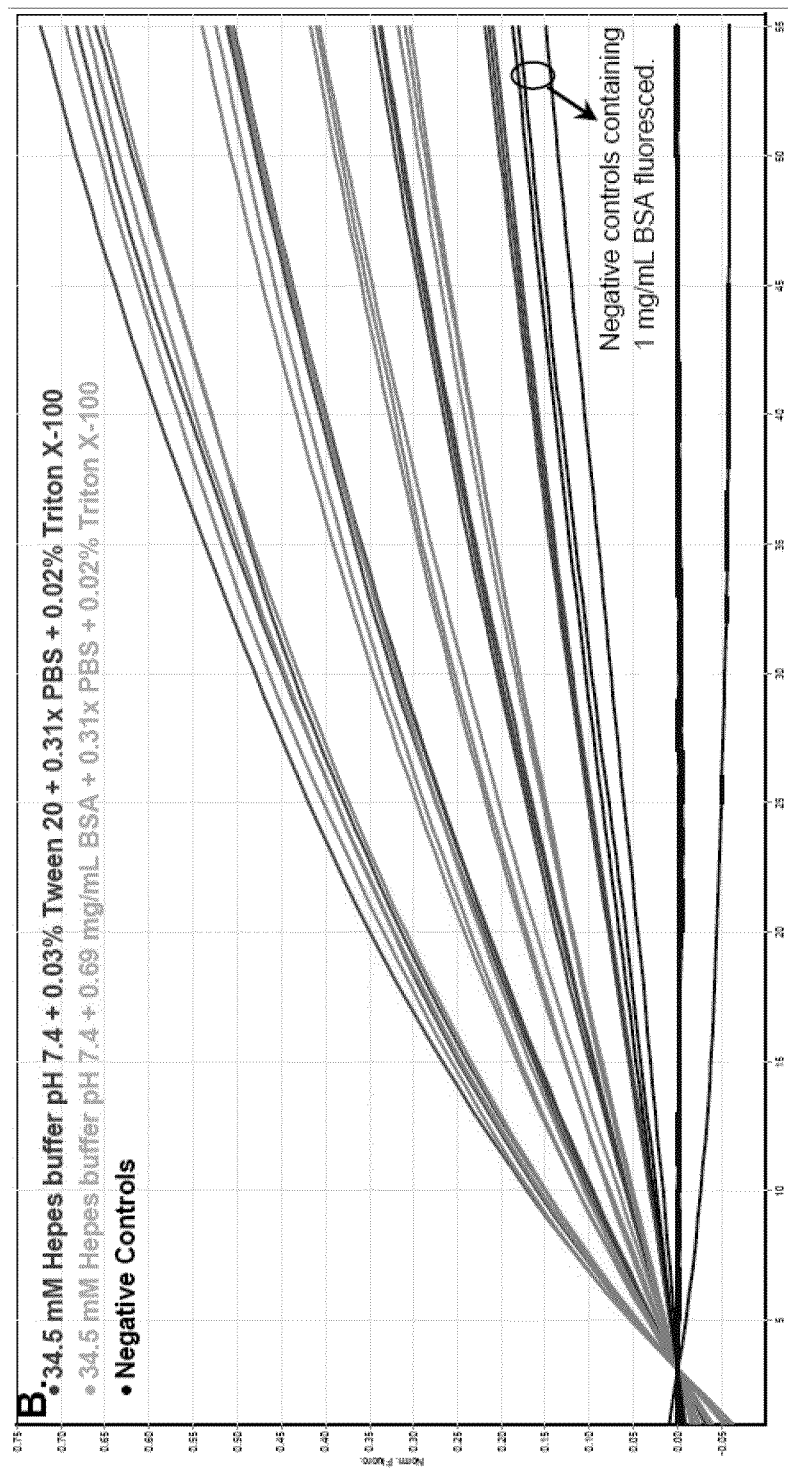

FIG. 3A-3B is a series of graphs displaying results acquired on the Rotor-Gene® Q qPCR instrument from the buffer optimization using 10 μM SNAPtide® and 1.9 ng, 3.8 ng, 7.5 ng, and 15 ng BoNT/A-LC.

Figure 4A:
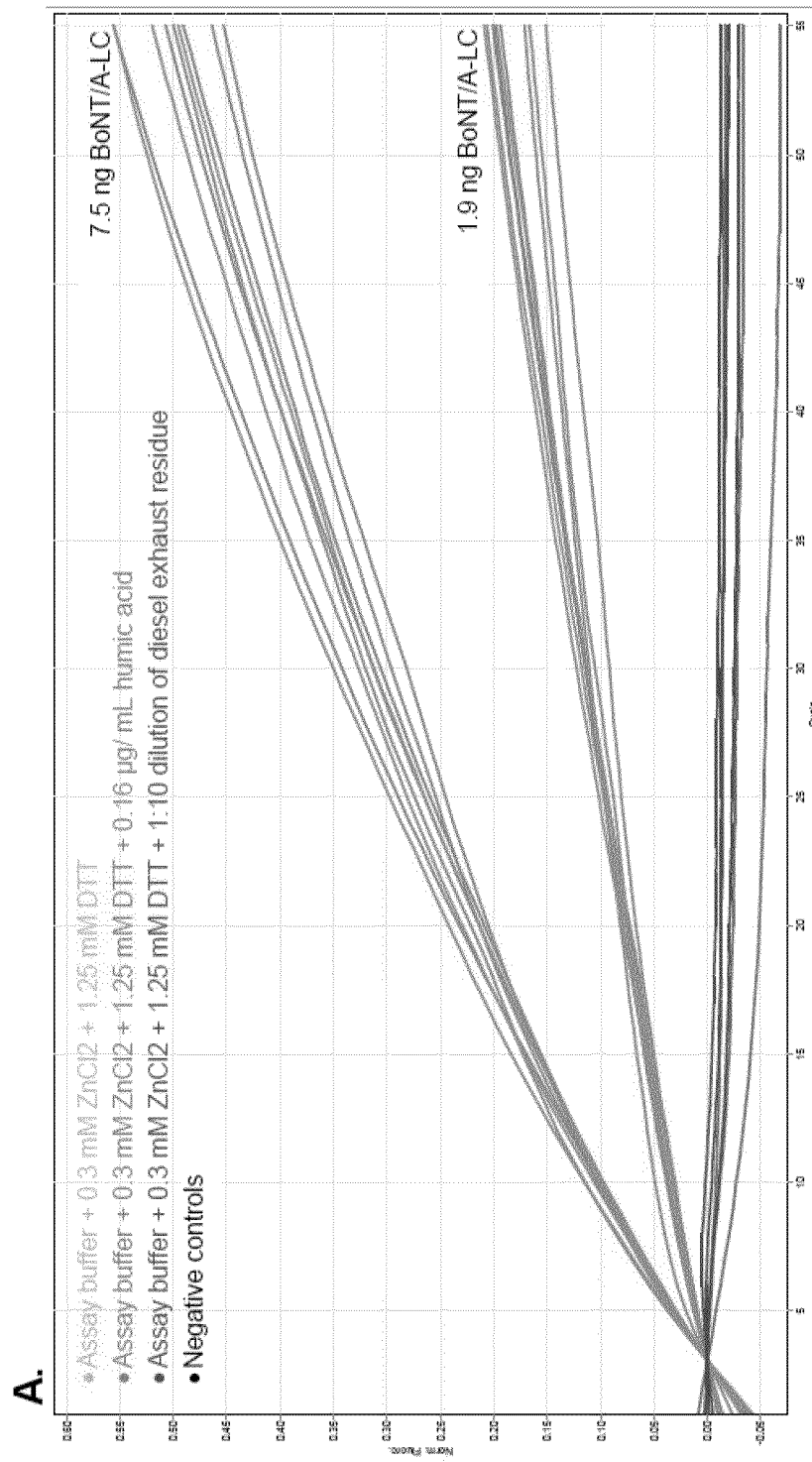
Figure 4B:
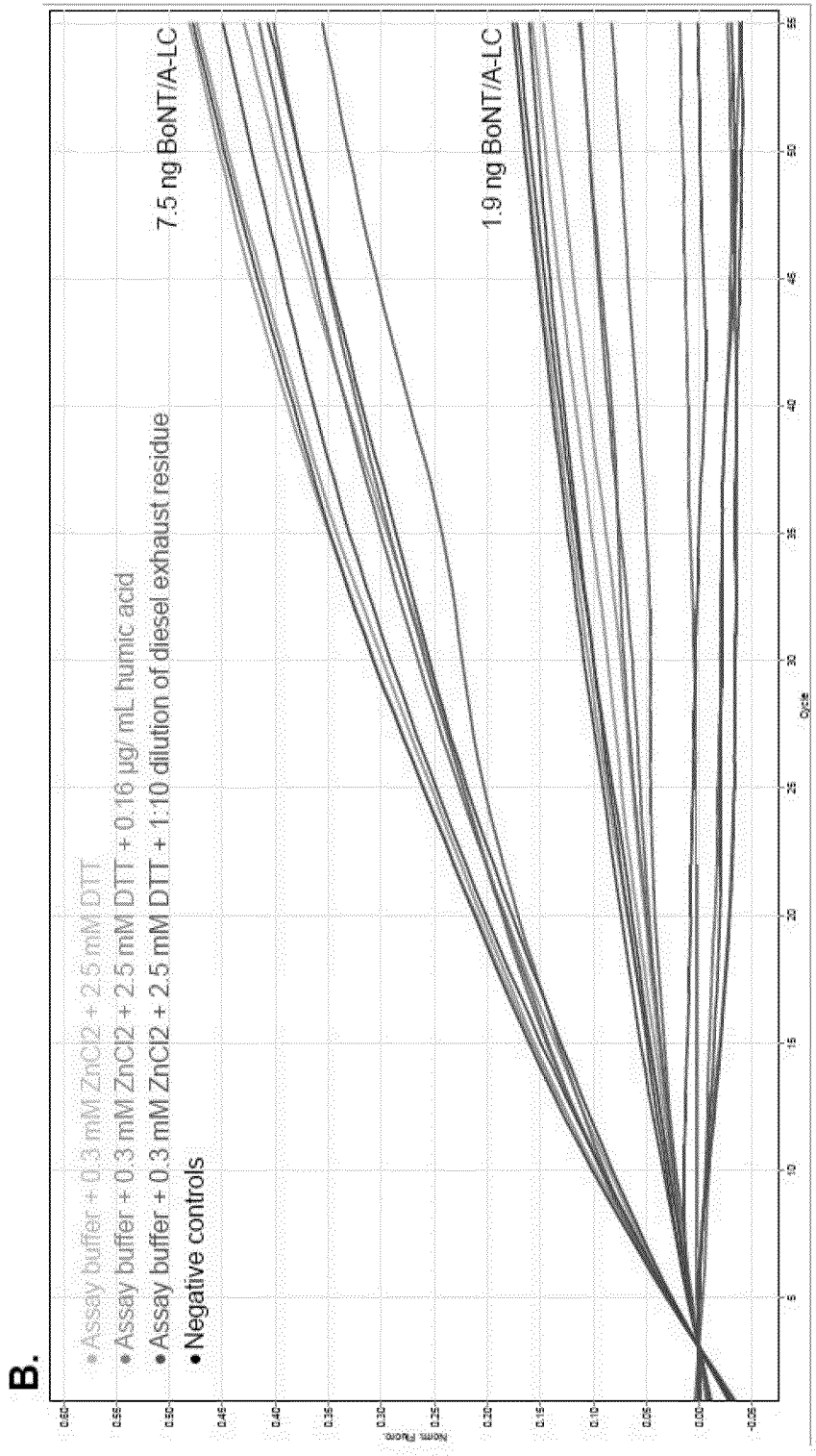
Figure 4C:
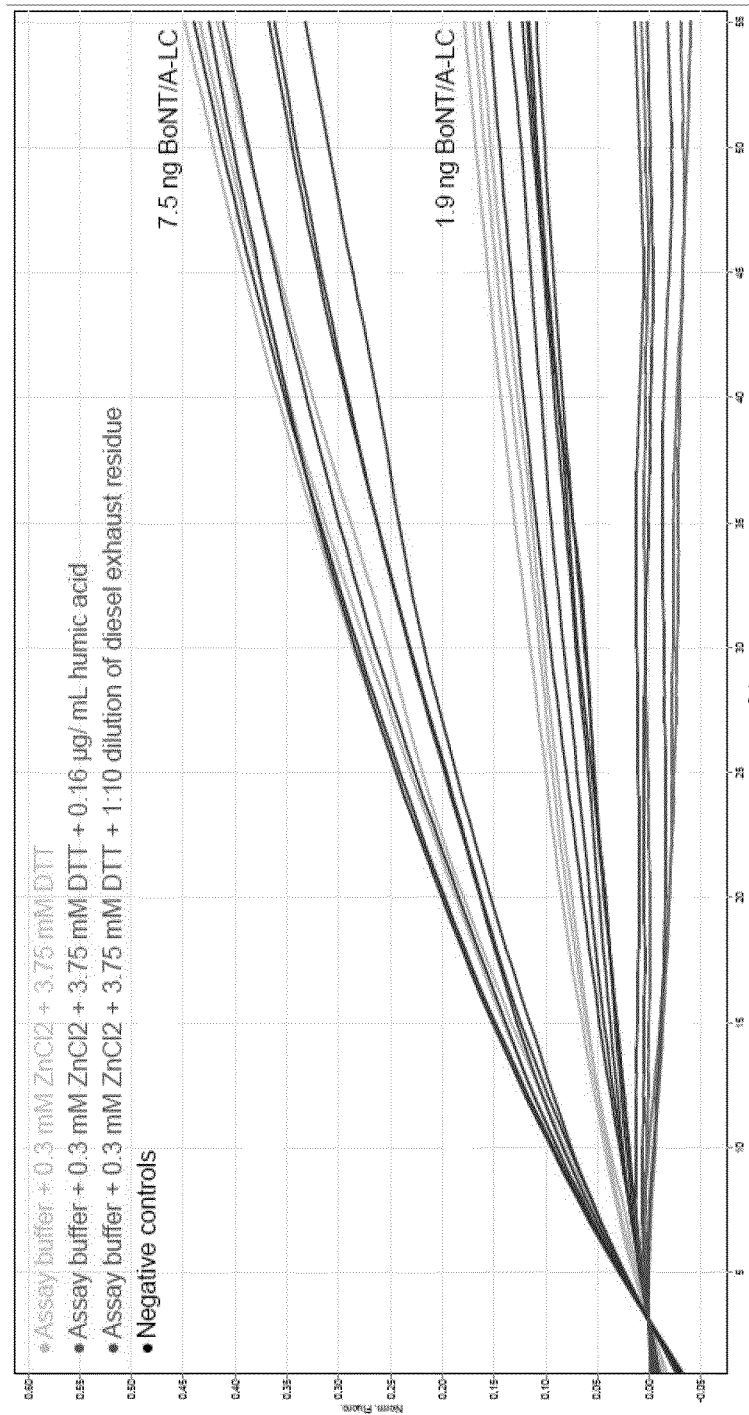

FIG. 4A-4C is a series of graphs displaying results acquired on the Rotor-Gene® Q qPCR instrument using 10 μM SNAPtide® showing the activity of 1.9 ng and 7.5 ng BoNT/A-LC in the presence of $ZnCl_2$ with varying concentrations of DTT and in the presence of the common PCR inhibitors humic acid or diesel exhaust residue.

Figure 5:
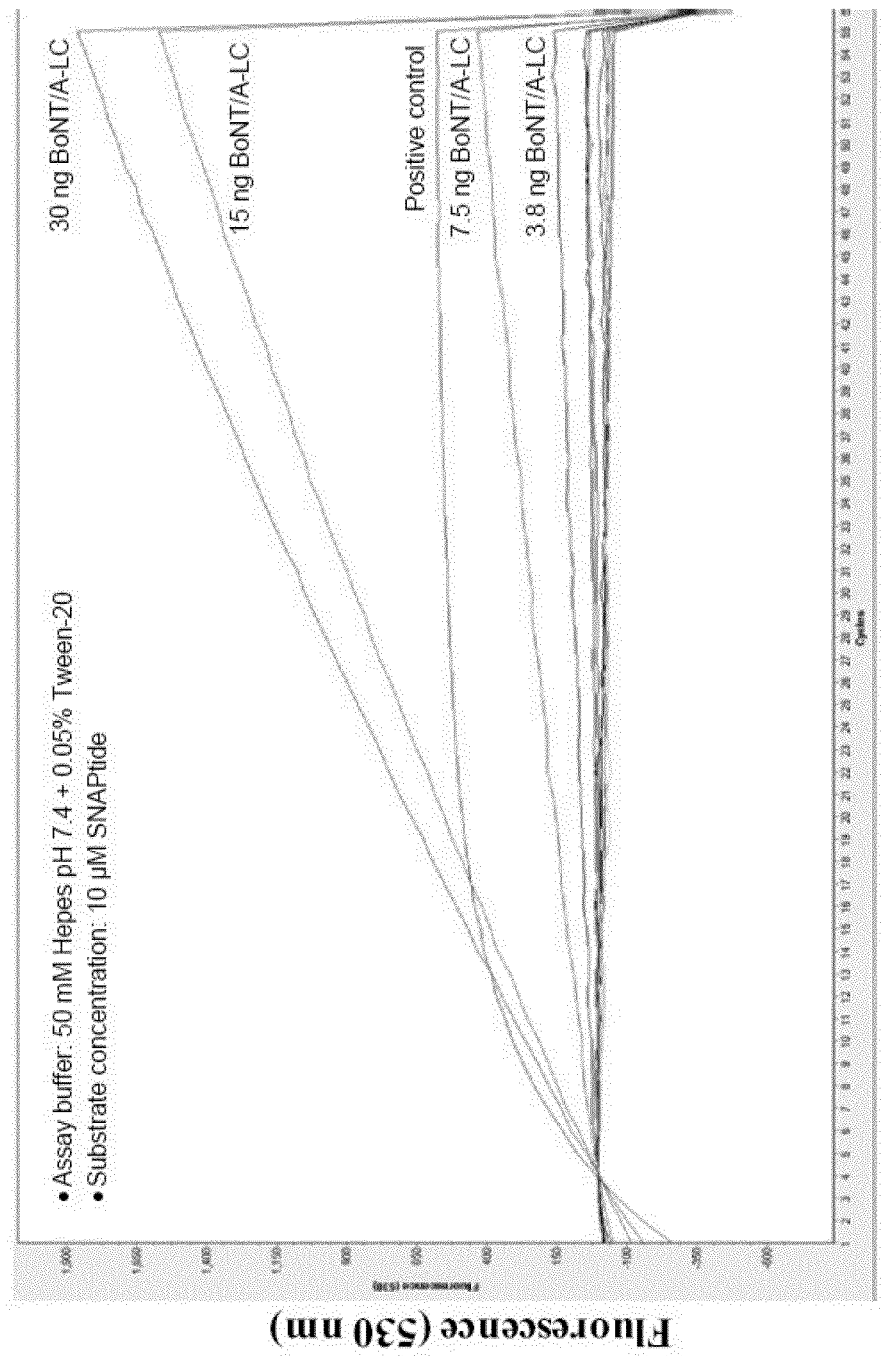

FIG. 5 is a graph displaying results acquired on the RAZOR® EX portable qPCR instrument using 10 μM SNAPtide® showing the activity of a range of BoNT/A-LC amounts (0.11 ng-30 ng) incubated for 55 minutes at 37° C.

Figure 6:
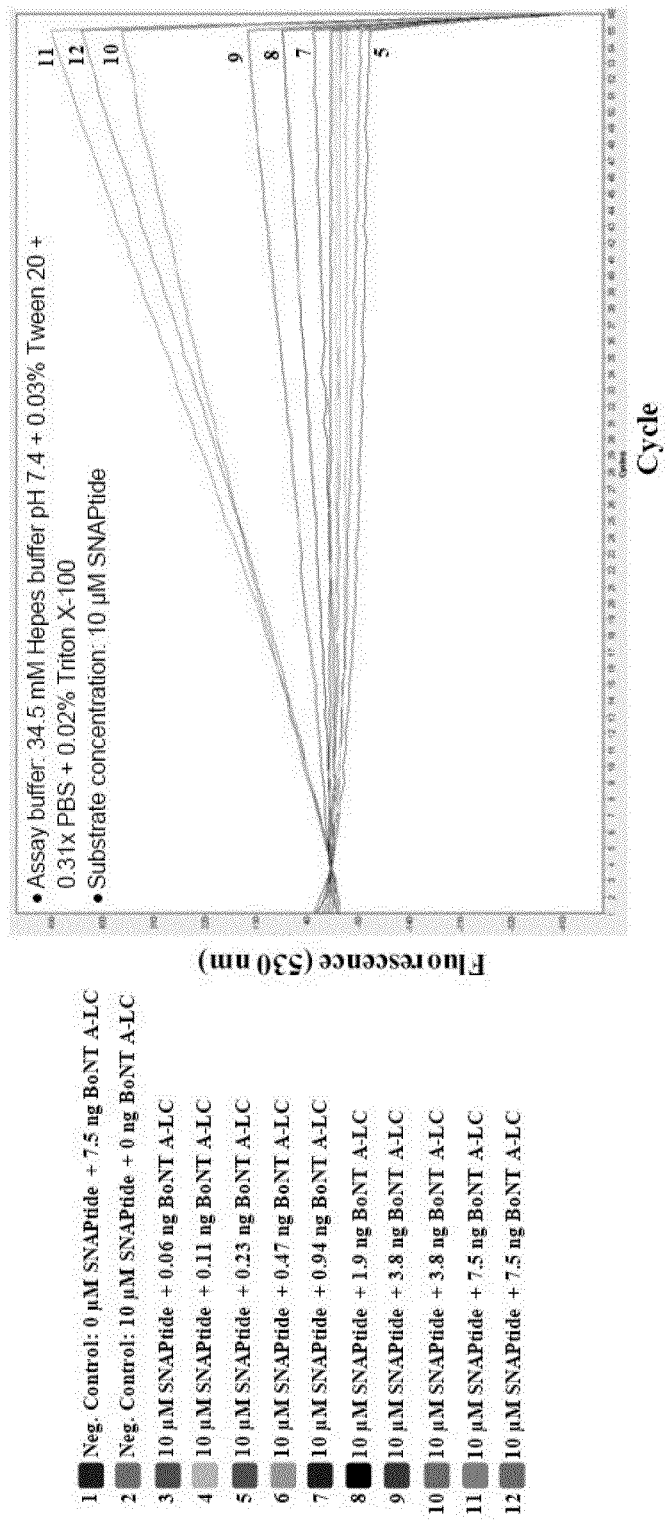

FIG. 6 is a graph displaying results acquired on the RAZOR® EX portable qPCR instrument using 10 μM SNAPtide® showing the activity of a range of BoNT/A-LC (0.06 ng-7.5 ng) using 34.5 mM Hepes buffer pH 7.4+0.03% (v/v) Tween 20+0.31% PBS+0.02% (v/v) Triton X-100.

Figure 7:
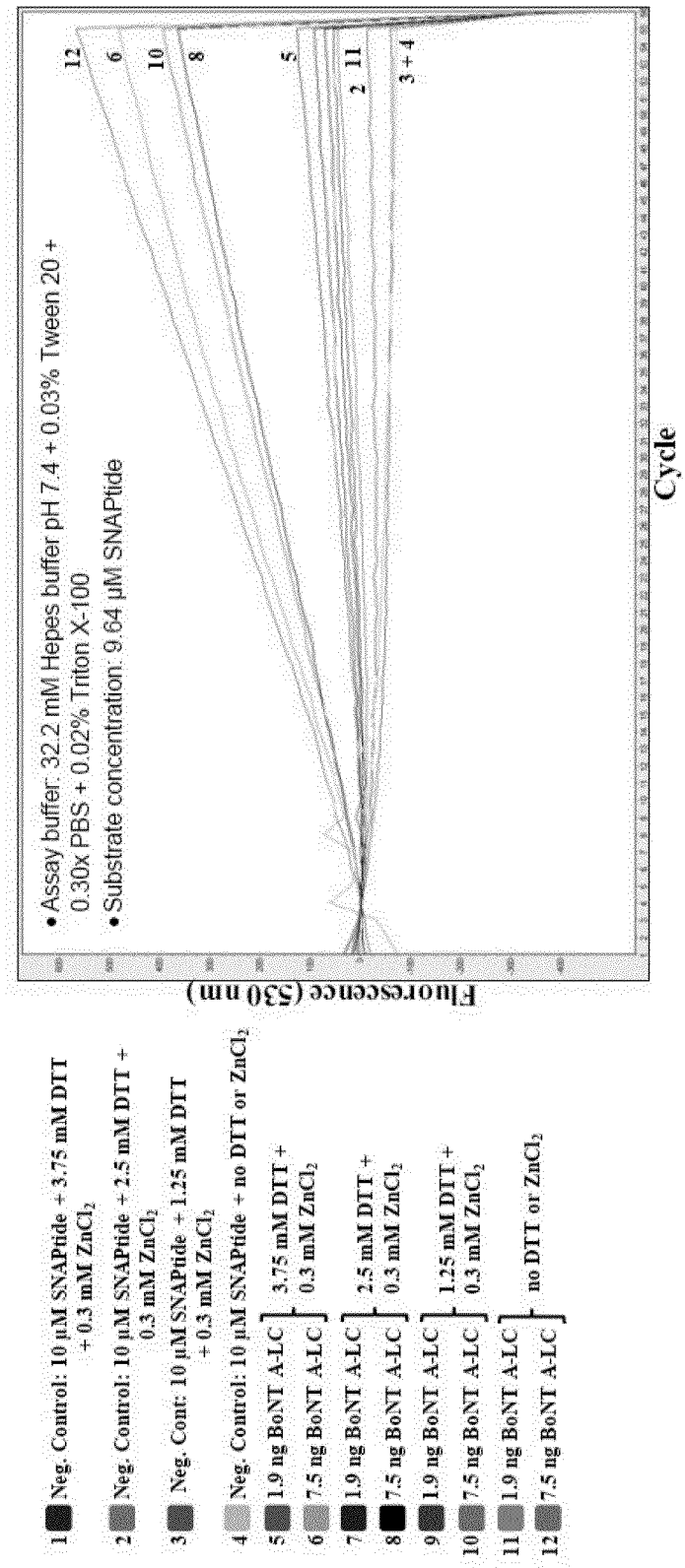

FIG. 7 is a graph displaying results acquired on the RAZOR® EX portable qPCR instrument using 10 μM SNAPtide® showing the optimization of $ZnCl_2$ and DTT concentrations in the BoNT/A-LC detection assay.

Figure 8:
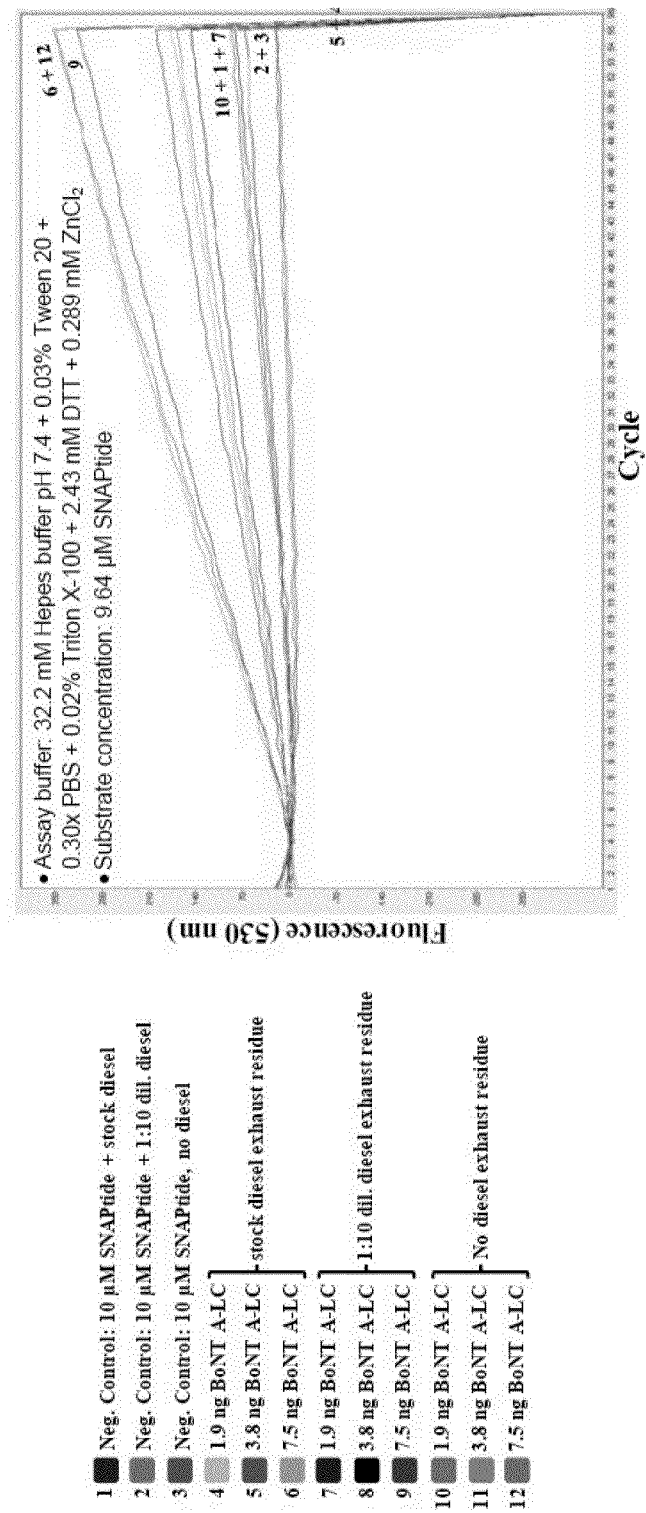

FIG. 8 is a graph displaying results acquired on the RAZOR® EX portable qPCR instrument using 10 μM SNAPtide® showing the detection of 1.9 ng-7.5 ng BoNT/A-LC in the presence of the common qPCR inhibitor diesel exhaust residue.

Figure 9:
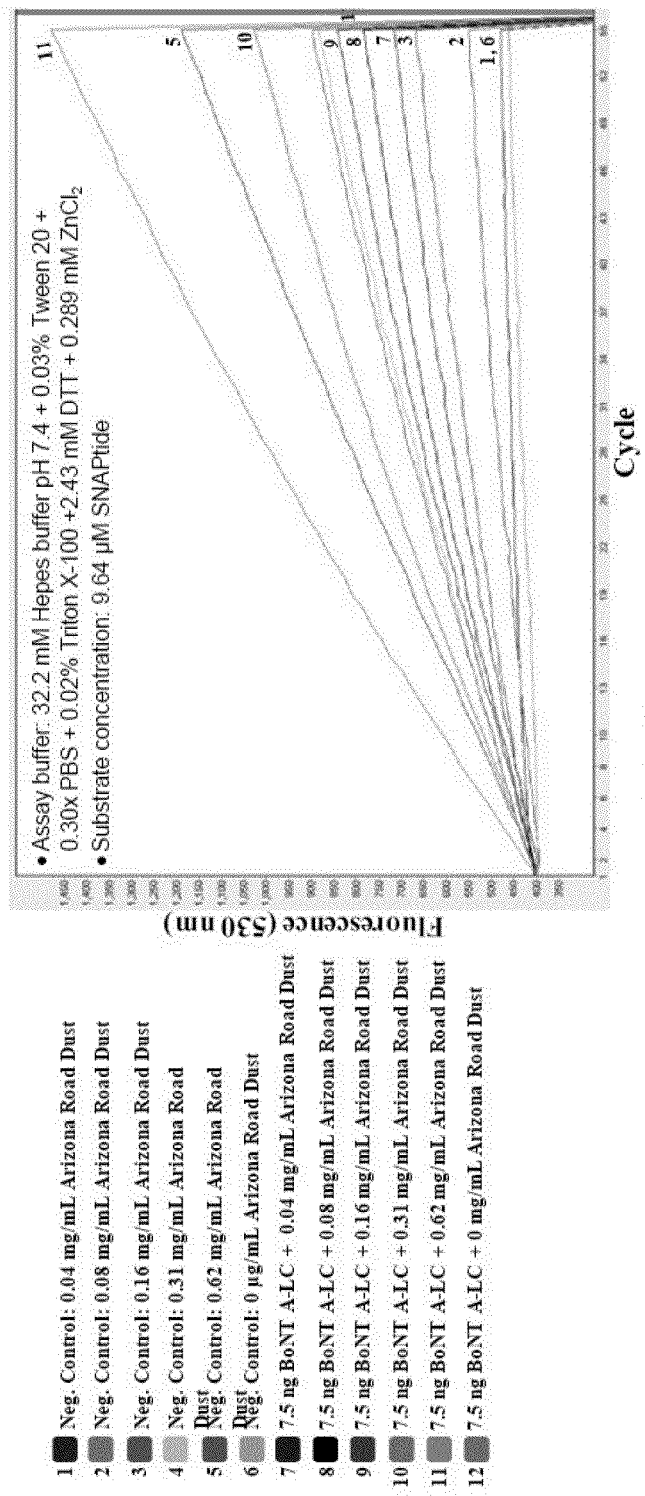

FIG. 9 is a graph displaying results acquired on the RAZOR® EX portable qPCR instrument using 10 μM SNAPtide® showing the detection of 7.5 ng BoNT/A-LC in the presence of the common qPCR inhibitor Arizona road dust.

Figure 10:
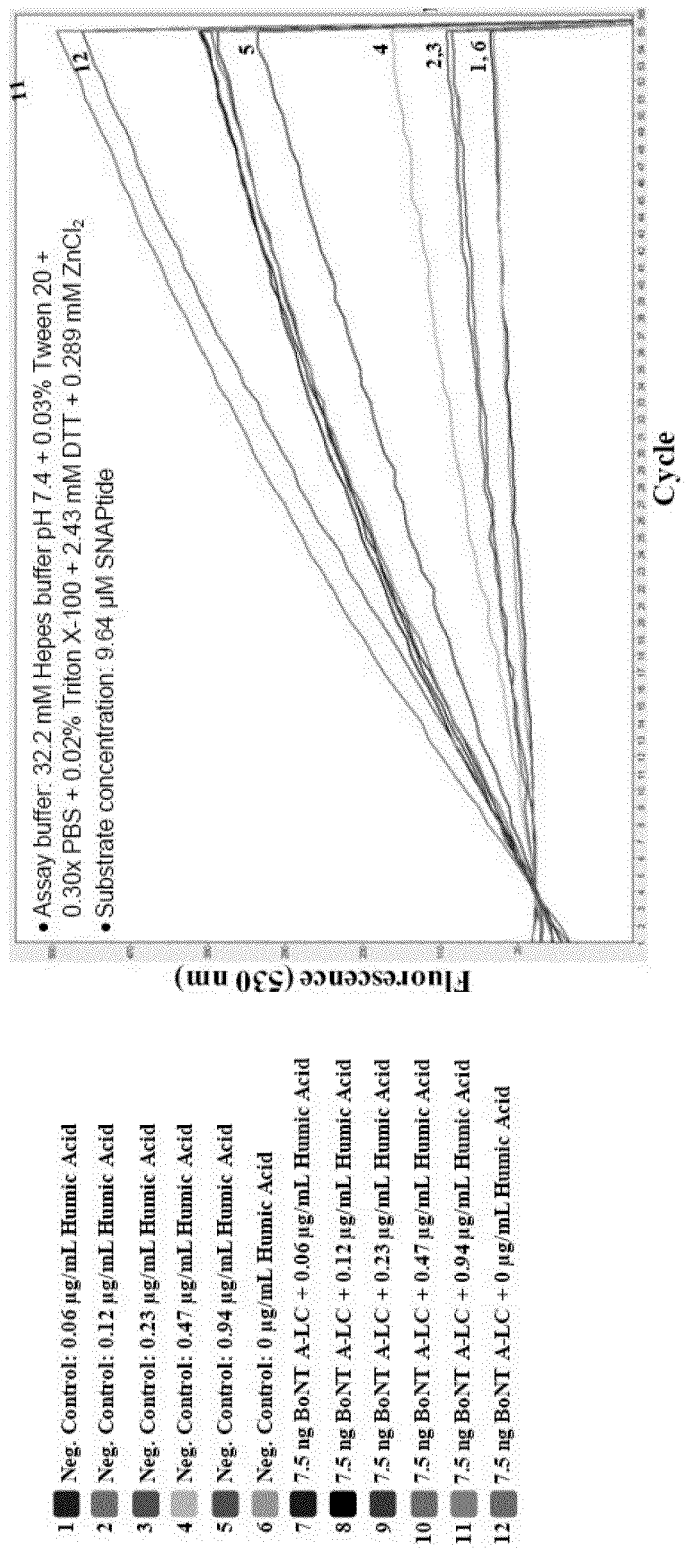

FIG. 10 is a graph displaying results acquired on the RAZOR® EX portable qPCR instrument using 10 μM SNAPtide® showing the detection 7.5 ng BoNT/A-LC in the presence of the common qPCR inhibitor humic acid.

FIG. 11A-11D shows three-dimensional graphical representations of the C-terminal region of SNAP-25 binding to BoNT/A-LC which aided in the design of a new BoNT/A peptide substrate.

Figure 12C:
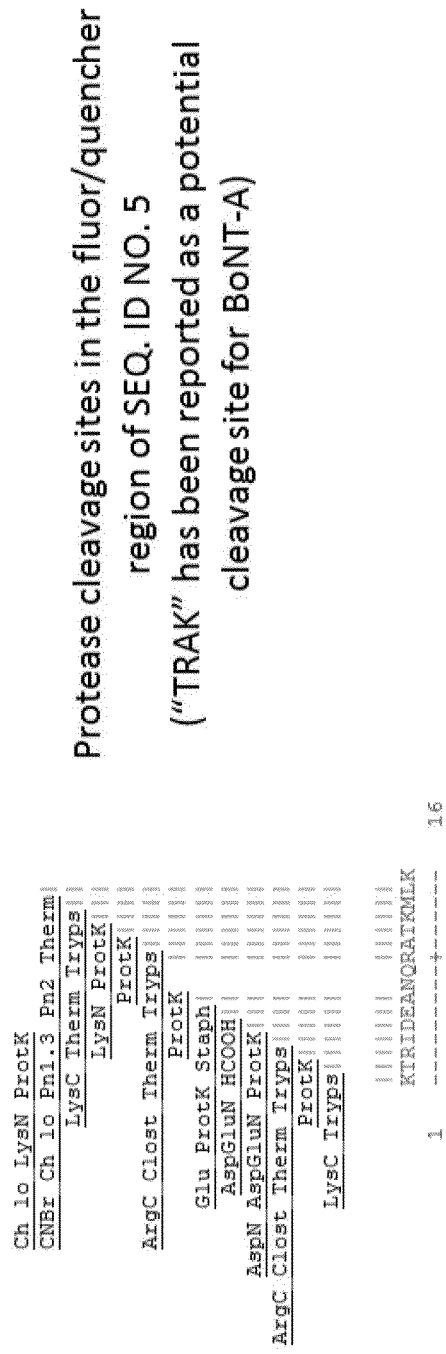

FIG. 12A-12C show the protease cleavage maps of newly designed BoNT/A peptide substrates.

Figure 13:
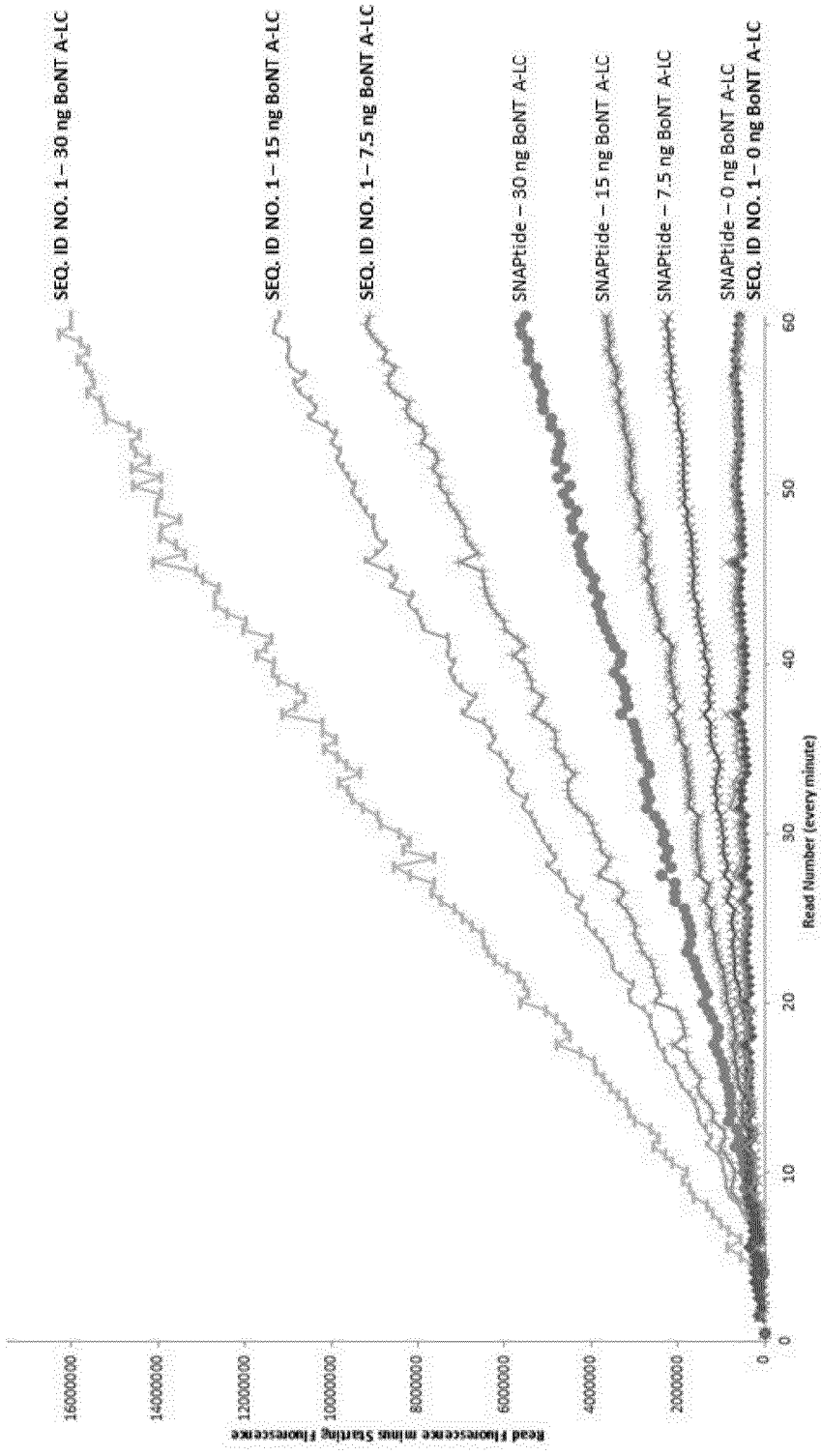

FIG. 13 is a graph displaying results acquired on the FilterMax® F5 fluorimeter using the newly designed SEQ. ID NO. 1 peptide substrate compared to SNAPtide® showing the improvement in detection of various amounts of BoNT/A-LC.

Figure 14:
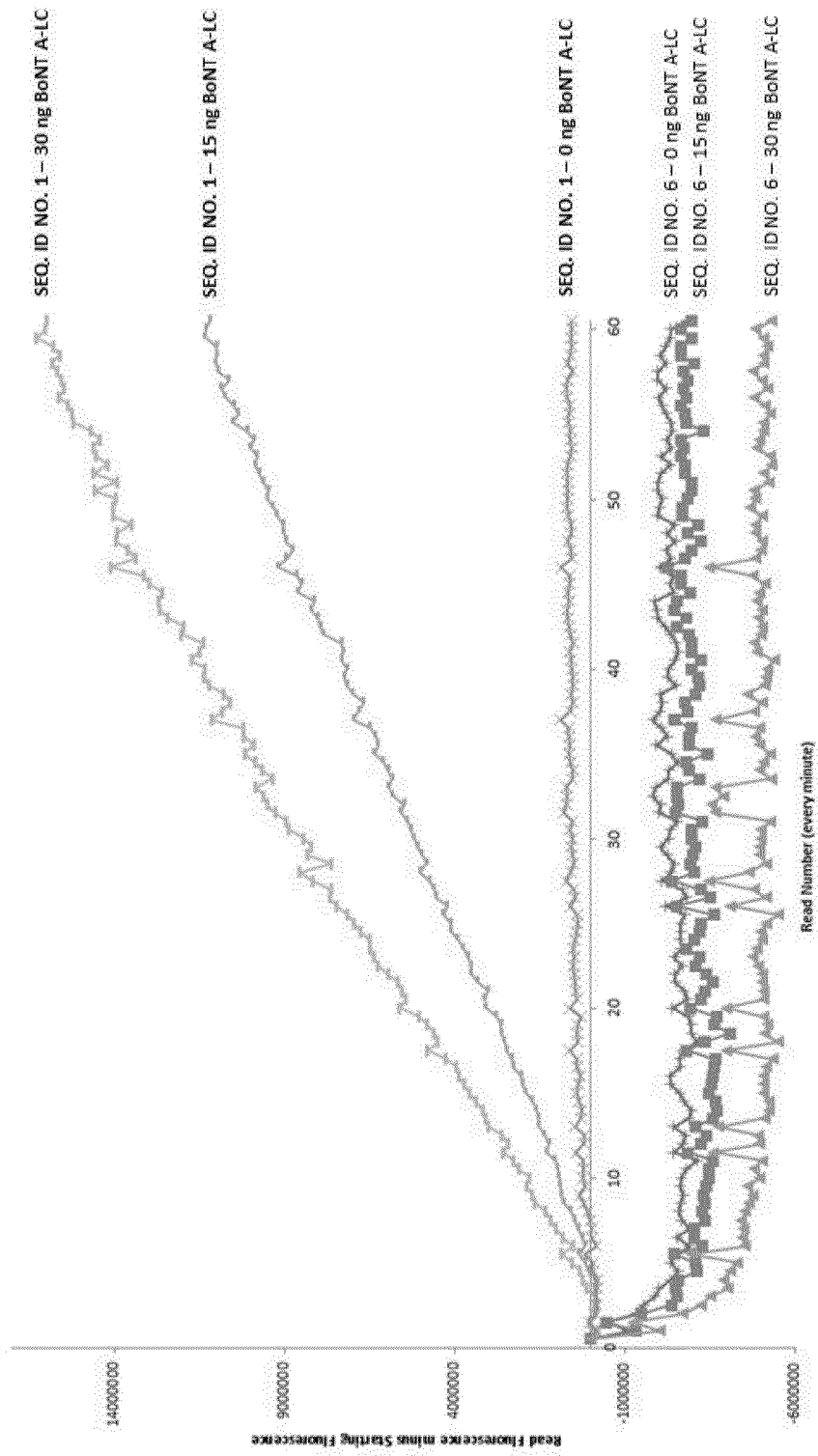

FIG. 14 is a graph displaying results acquired on the FilterMax® F5 fluorimeter showing the requirement of the SNARE domain in SEQ. ID NO. 1 (compared to SEQ. ID NO. 6) in the detection of BoNT/A-LC.

Figure 15A:
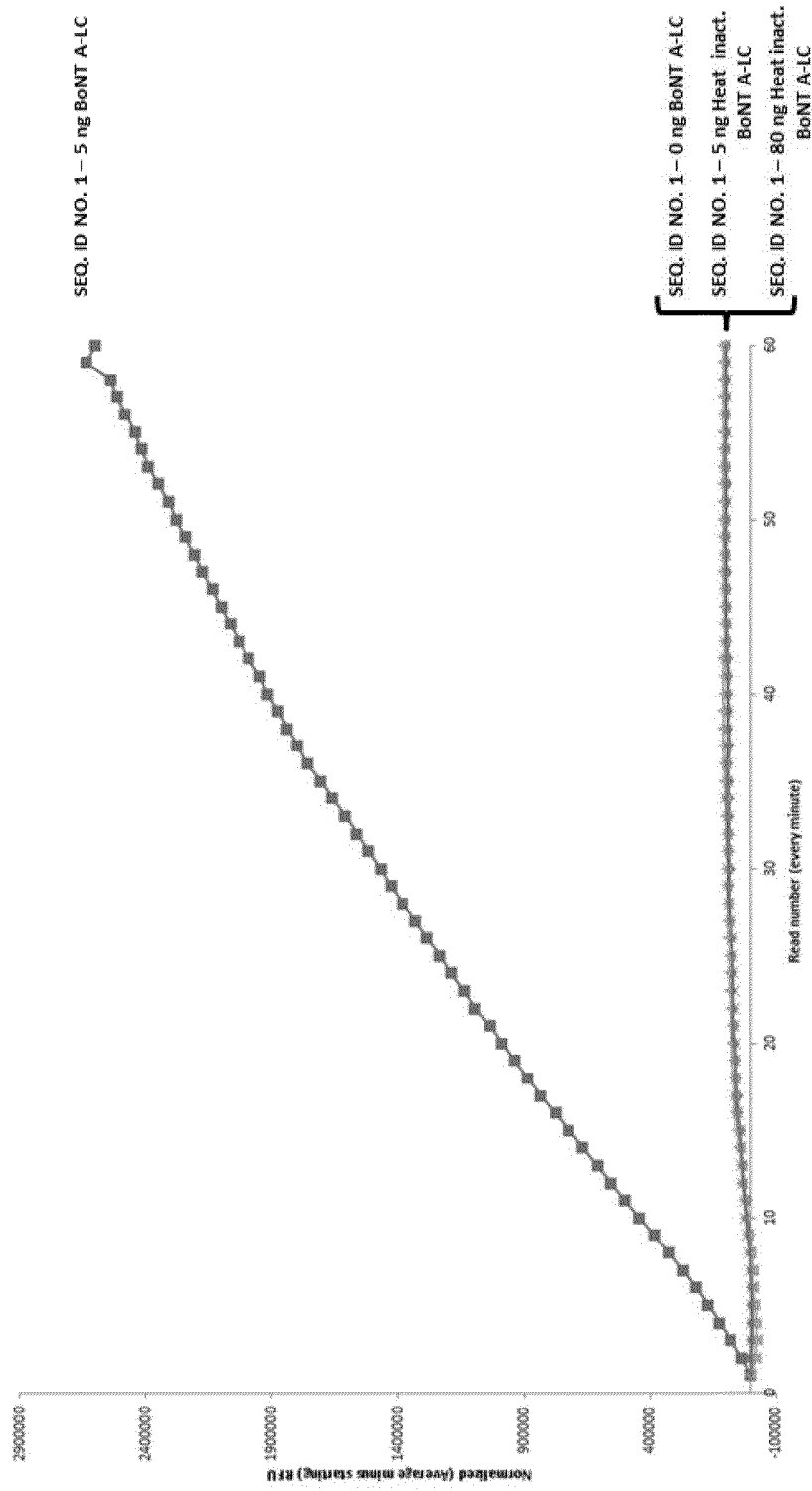
Figure 15B:
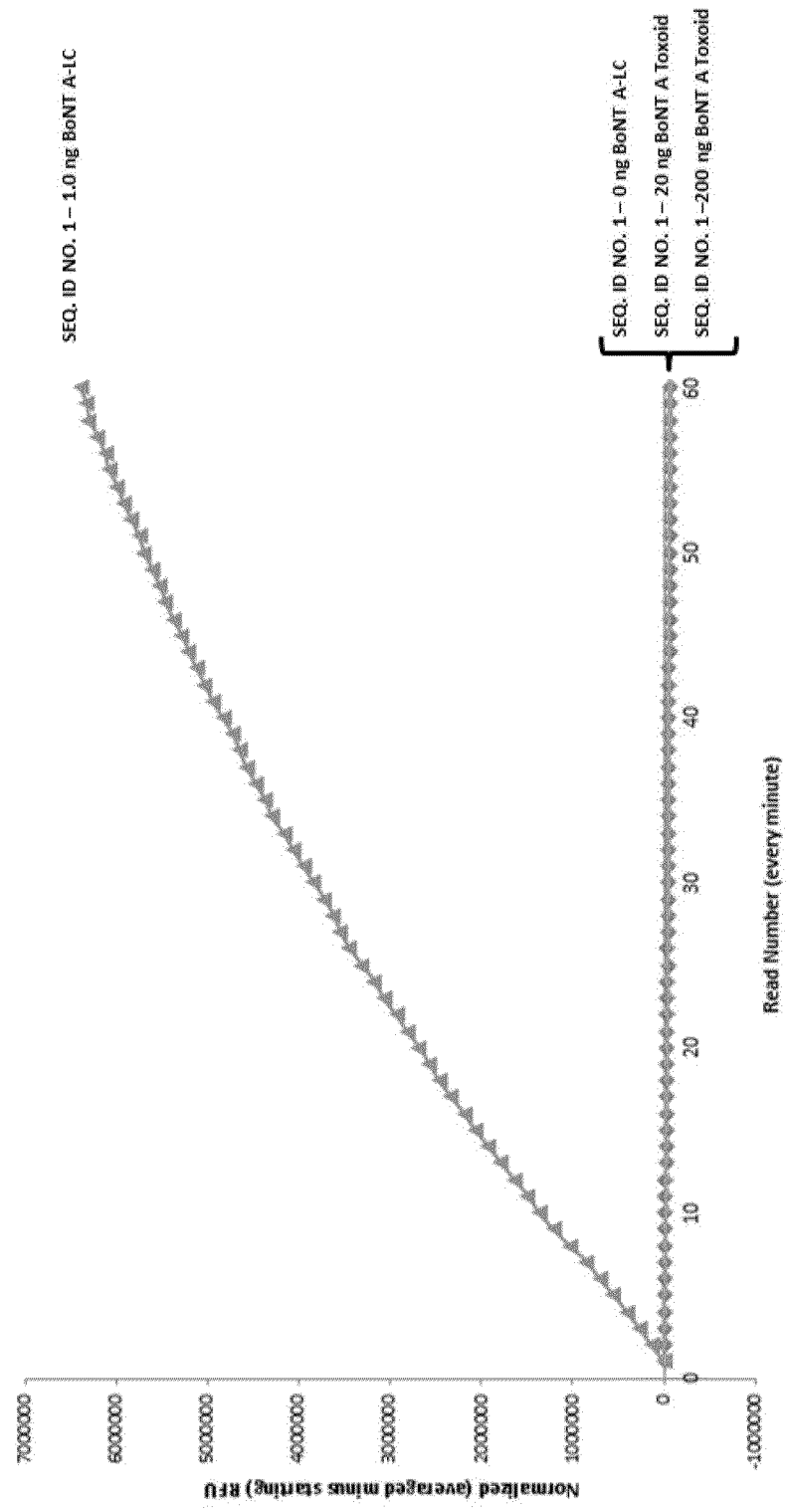

FIG. 15A-15B shows graphs displaying results acquired on the FilterMax® F5 fluorimeter showing that only biologically active BoNT/A is detected by the SEQ. ID NO. 1 BoNT/A peptide substrate.

Figure 16A:
Figure 16B:
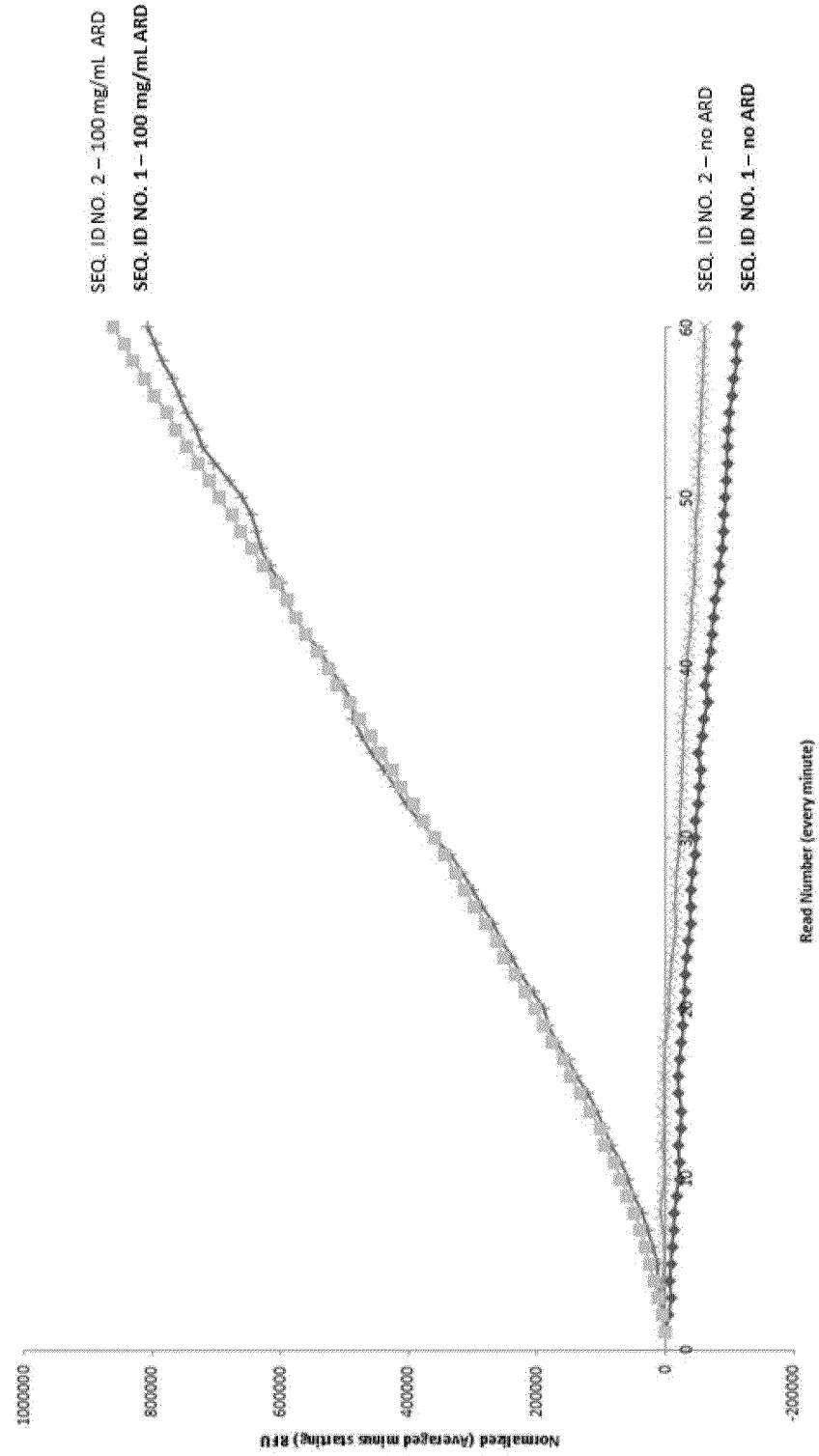

FIG. 16A-16B shows graphs displaying results acquired on the FilterMax® F5 showing that the SEQ. ID NO. 2 peptide substrate can act as a negative control/interferents sensor for SEQ. ID NO. 1 as it is unresponsive to biologically active BoNT/A-LC, but can detect non-specific protease activity (such as that found in Arizona Road Dust).

Figure 17:
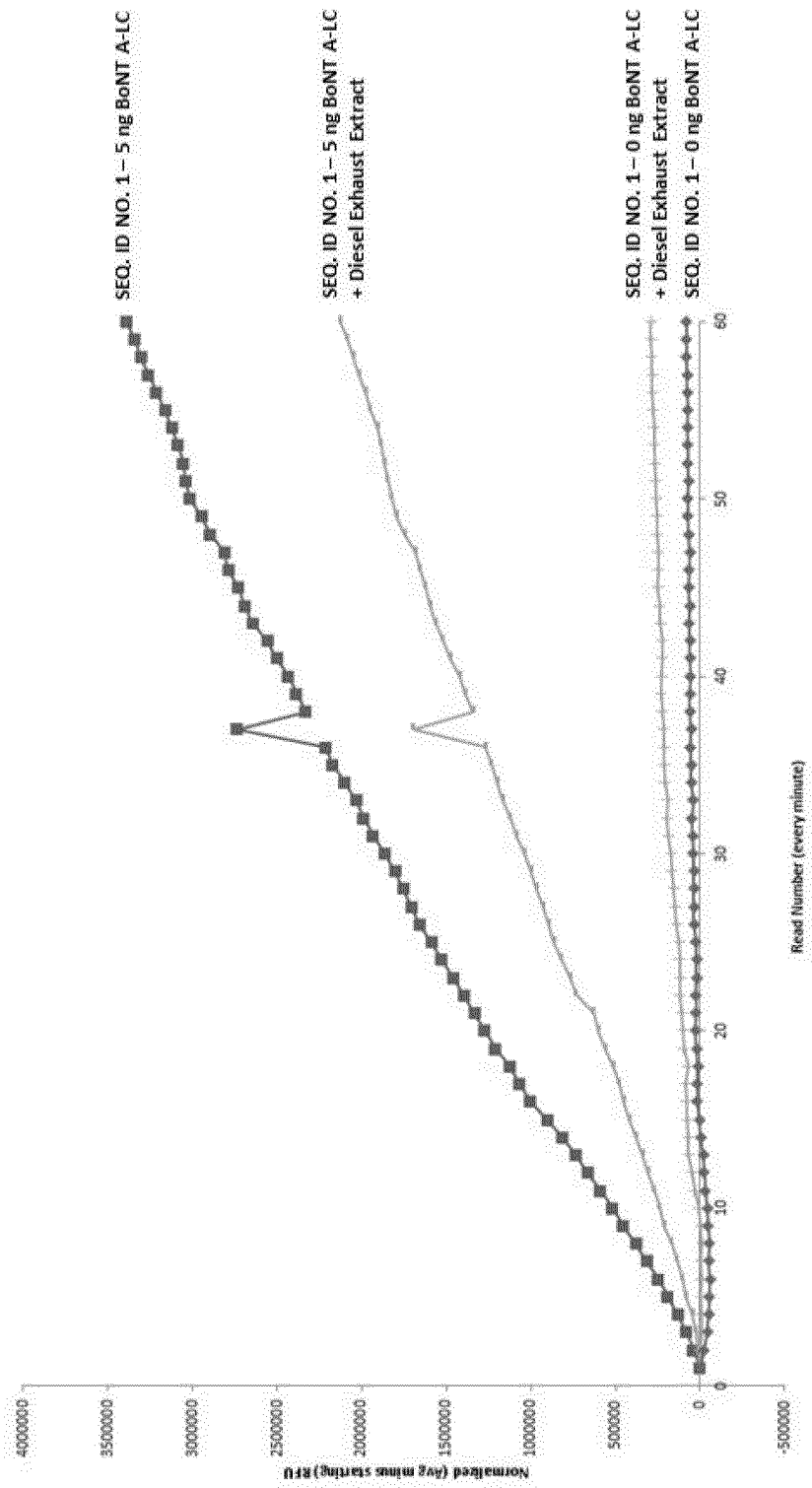

FIG. 17 is a graph displaying results acquired on the FilterMax® F5 using SEQ. ID NO. 1 showing the detection of 5.0 ng BoNT/A-LC in the presence of the common PCR inhibitor diesel exhaust extract.

Figure 18:

FIG. 18 is a graph displaying results acquired on the FilterMax® F5 using SEQ. ID NO. 1 showing the detection of 2.5 ng BoNT/A-LC in the presence of the common PCR inhibitor humic acid.

Figure 19:
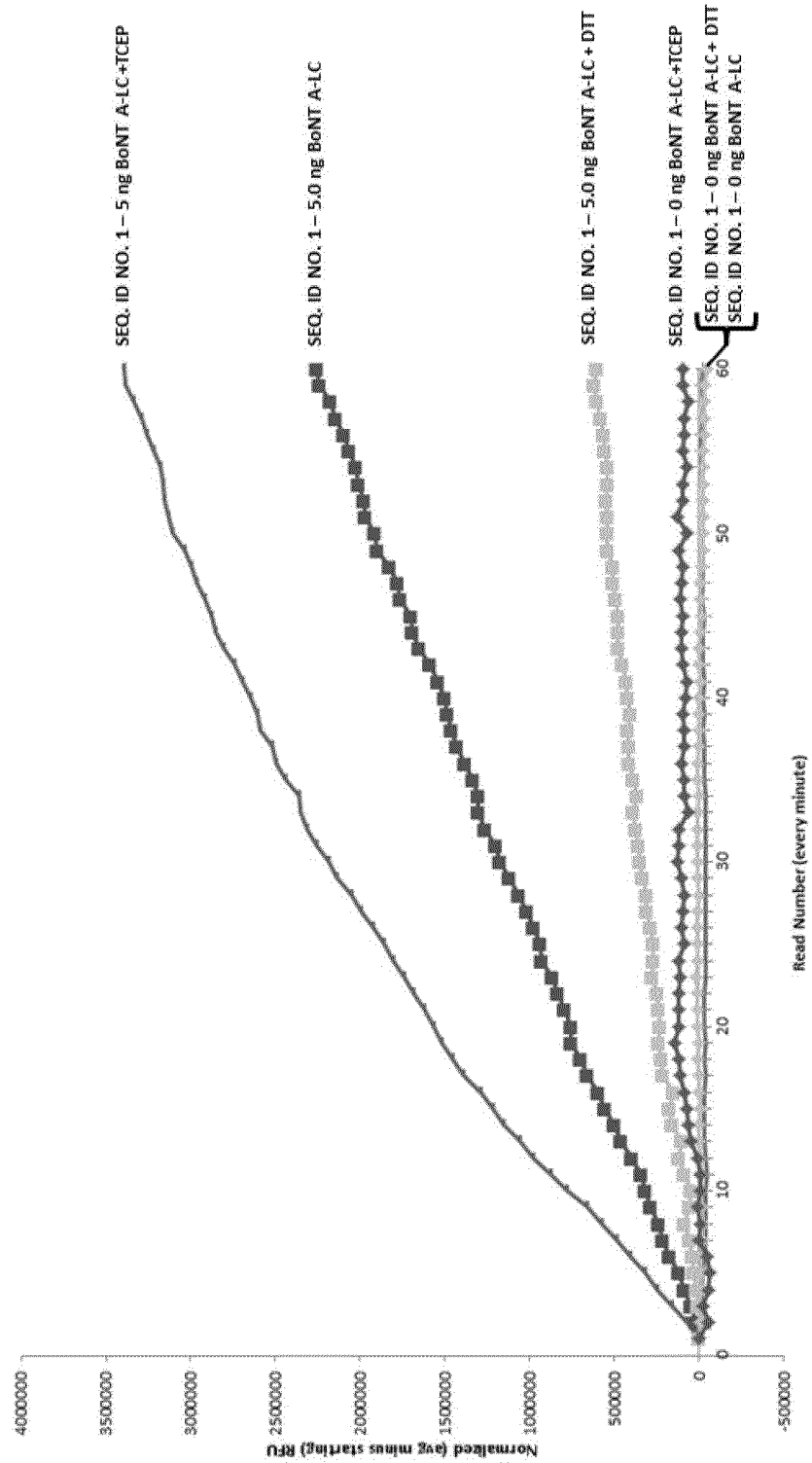

FIG. 19 is a graph displaying results acquired on the FilterMax® F5 using SEQ. ID NO. 1 showing the detection of 5.0 ng BoNT/A-LC in the presence of the reducing reagents TCEP and DTT.

Figure 20:
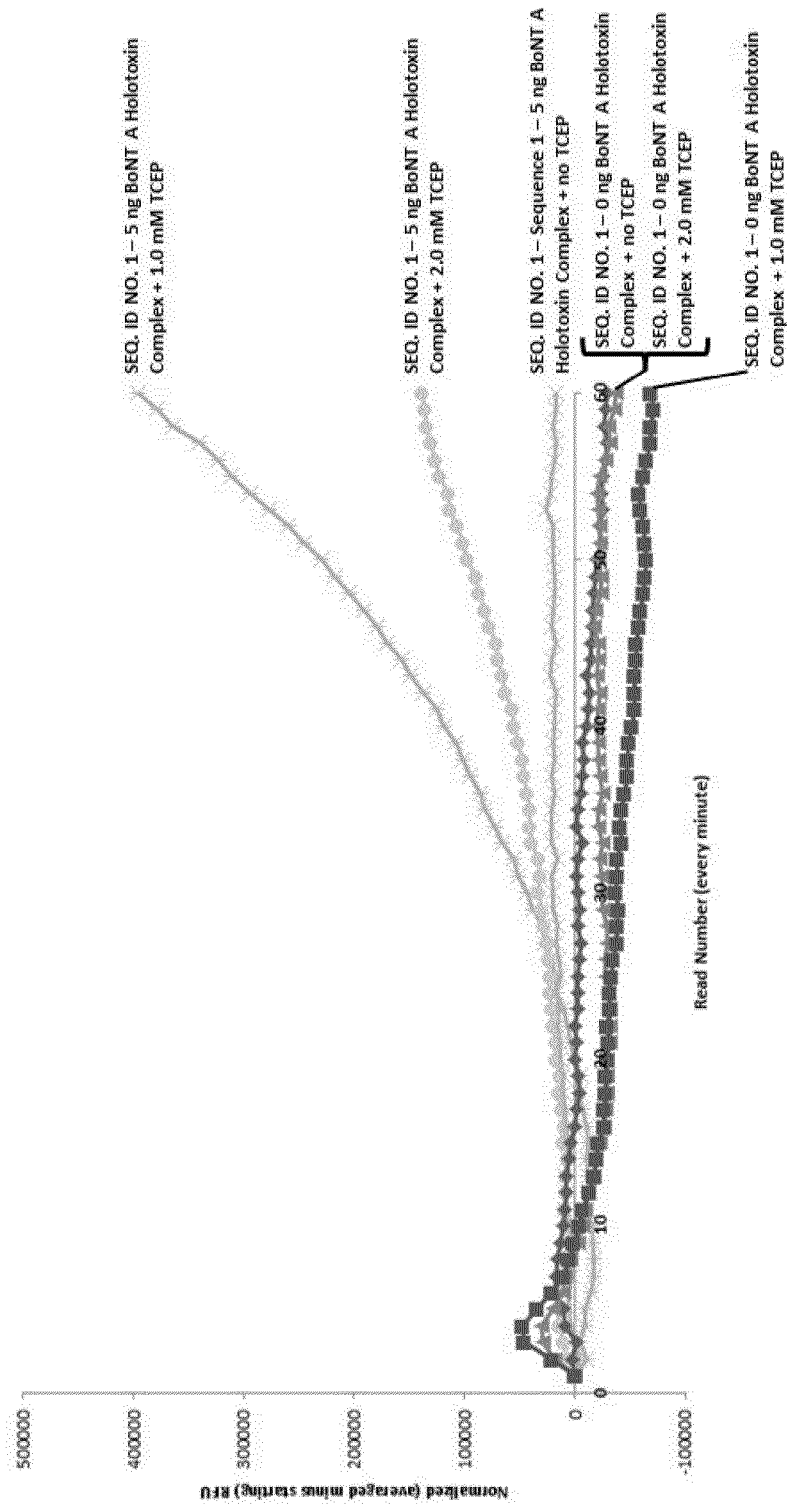

FIG. 20 is a graph displaying results acquired on the FilterMax® F5 using SEQ. ID NO. 1 showing the detection of 5.0 ng BoNT A Holotoxin Complex in the presence of varying concentrations of TCEP.

Figure 21:
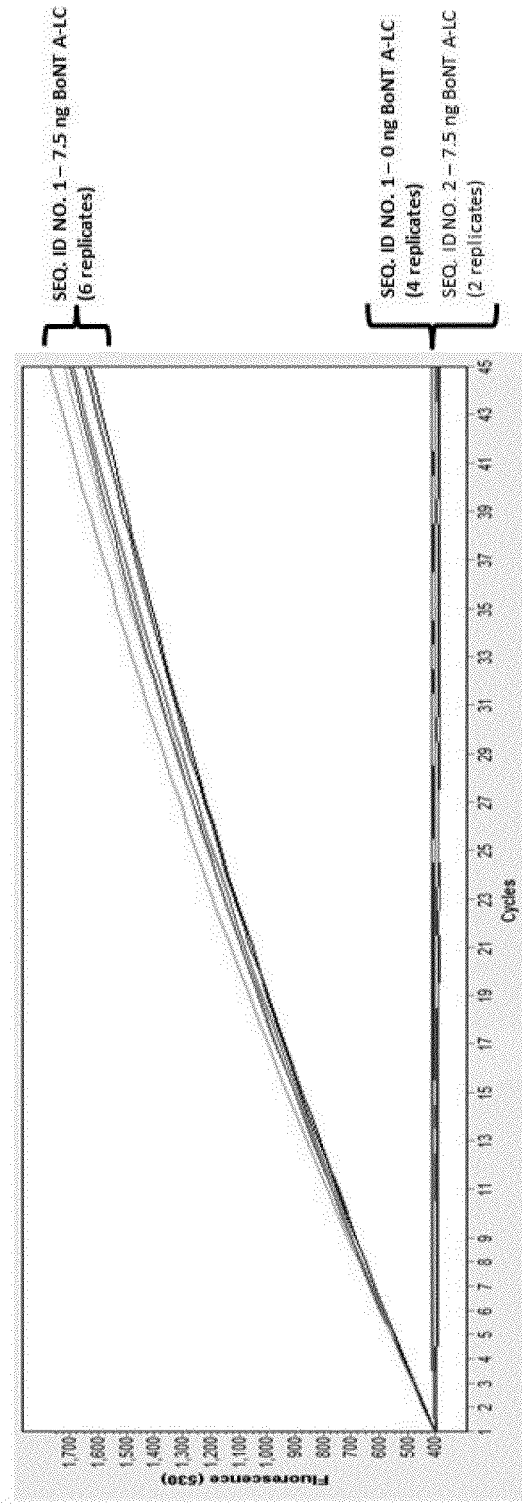

FIG. 21 is a graph displaying results acquired on the RAZOR® EX portable qPCR instrument using SEQ. ID NO. 1 and SEQ. ID NO. 2 showing the detection of 7.5 ng of BoNT/A-LC.

Figure 22:
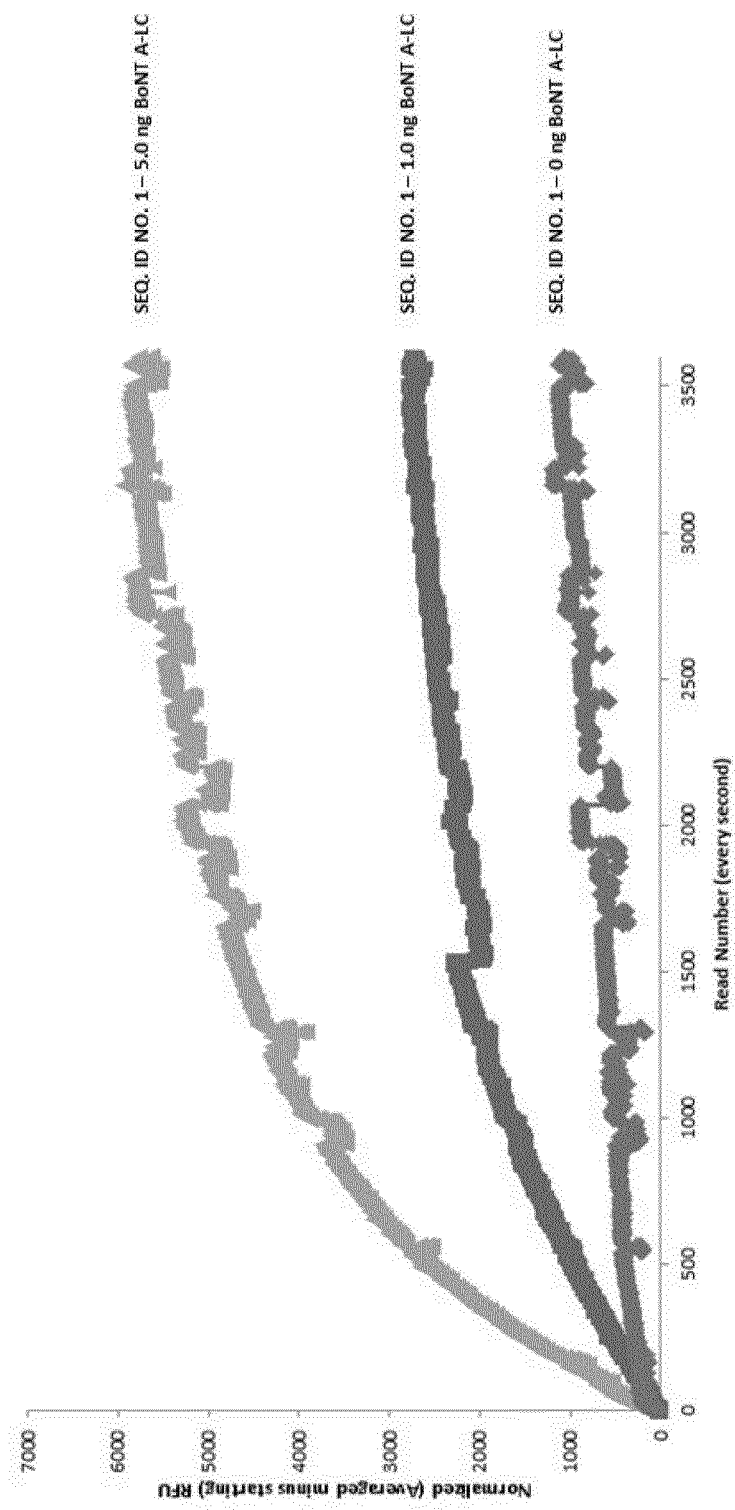

FIG. 22 is a graph displaying results acquired on the Genedrive® portable qPCR instrument using SEQ. ID NO. 1 showing the detection various amounts of BoNT/A-LC.

Figure 23:
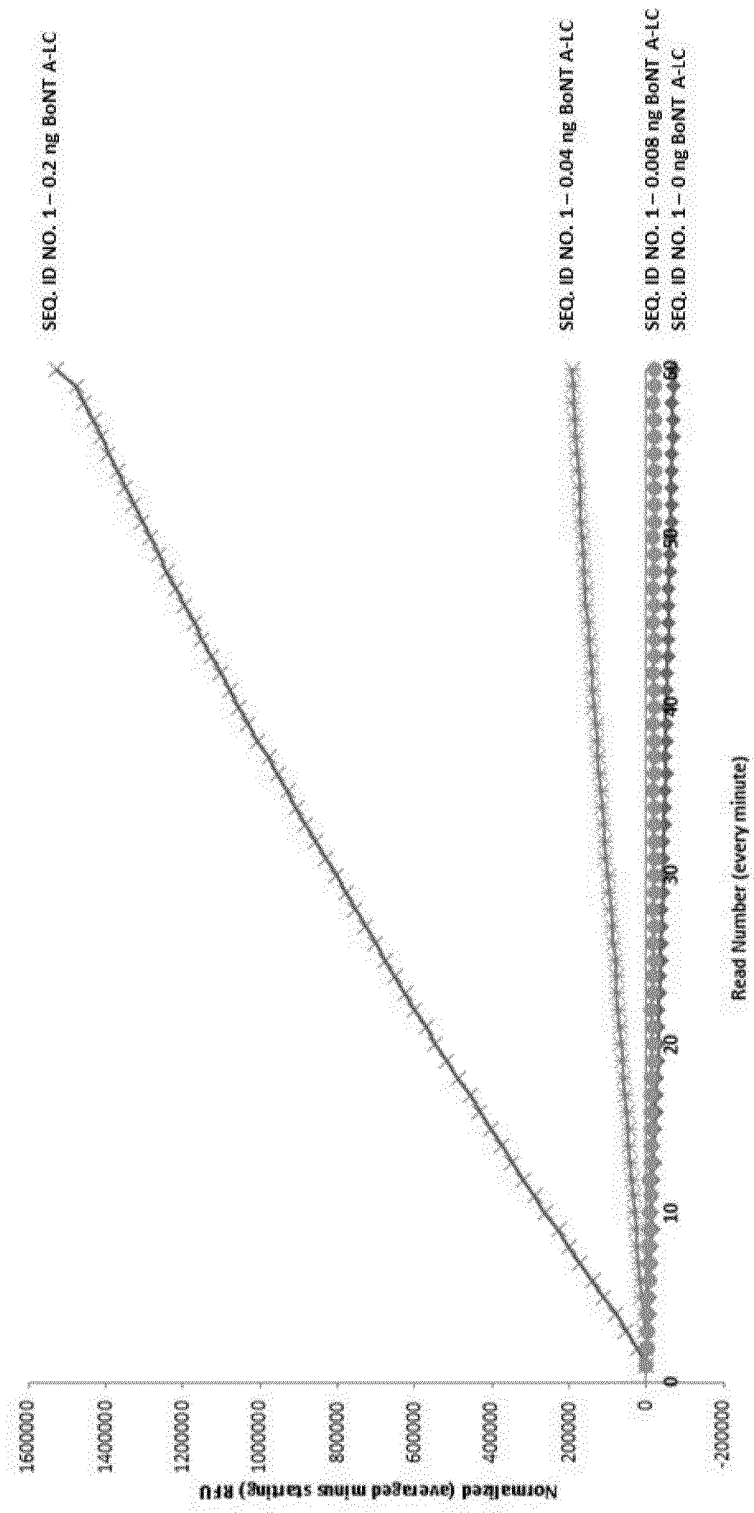

FIG. 23 is a graph displaying results acquired on the FilterMax® F5 using SEQ. ID NO. 1 showing the limits of detection of BoNT/A-LC.

FIG. 24 is a list of the formulas used in the detection algorithm of the present invention.

Figure 25:
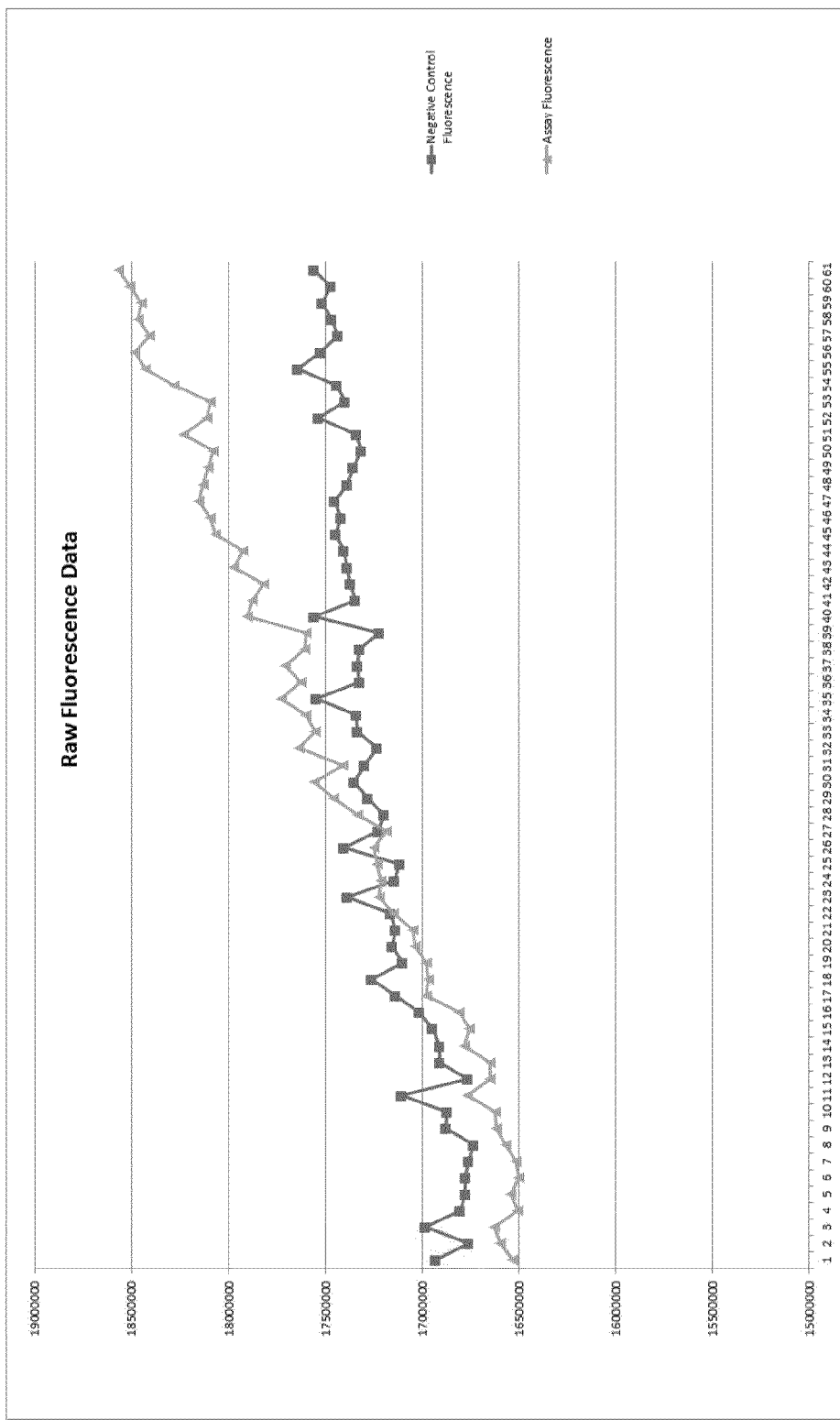

FIG. 25 is a graph of the raw data of an example according to the detection algorithm of the present invention.

Figure 26:
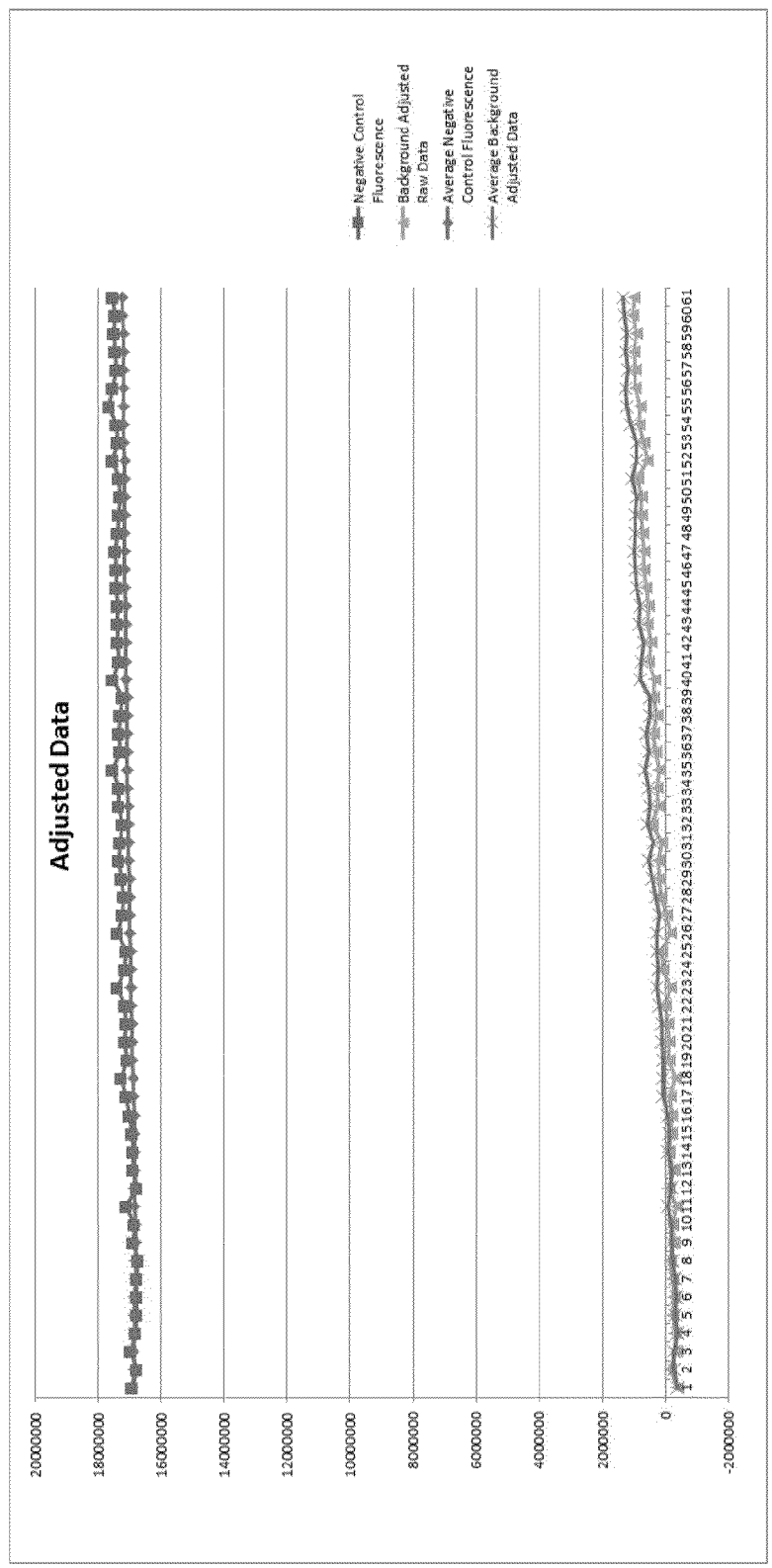

FIG. 26 is a graph of the adjusted raw data of an example according to the detection algorithm of the present invention.

Figure 27:
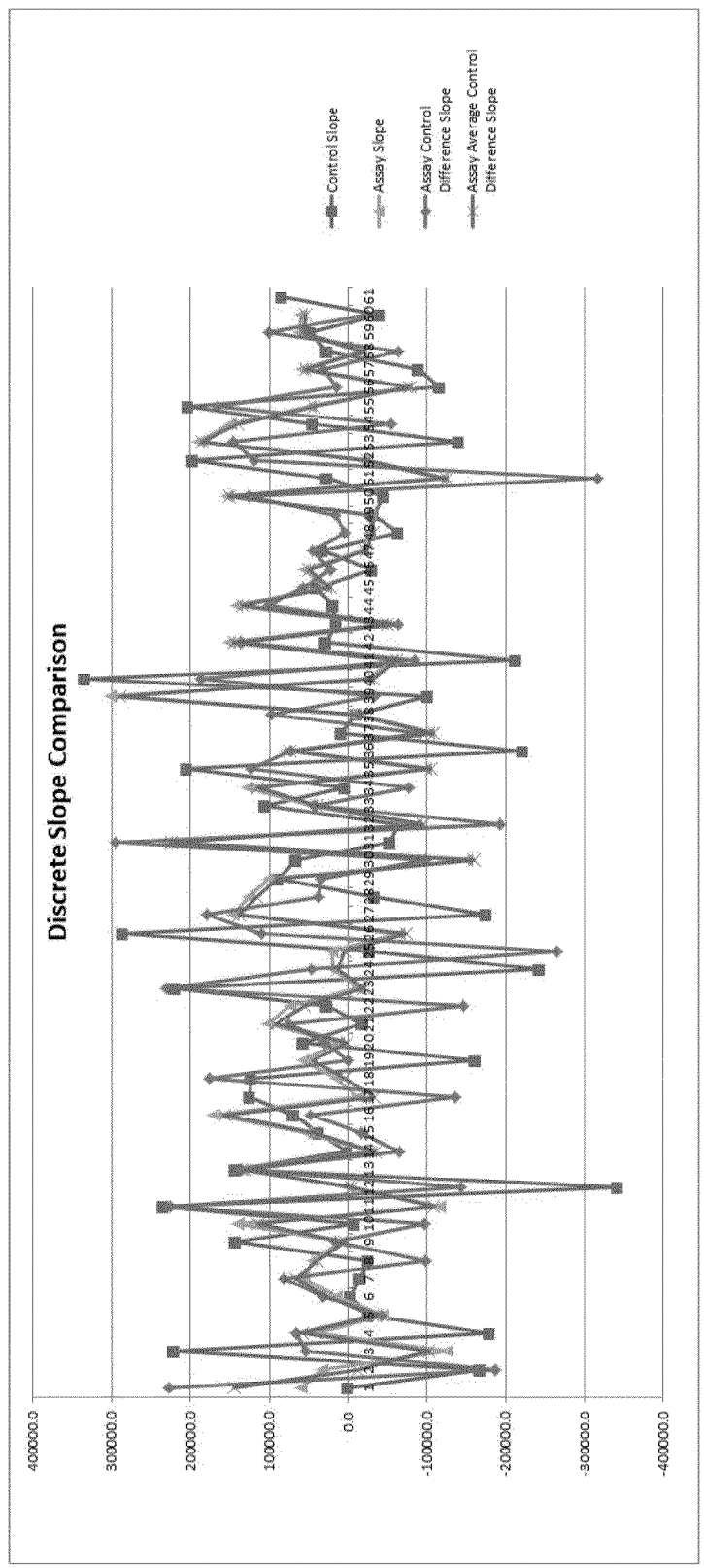

FIG. 27 is a graph of a discrete slope comparison according to the detection algorithm of the present invention.

Figure 28:
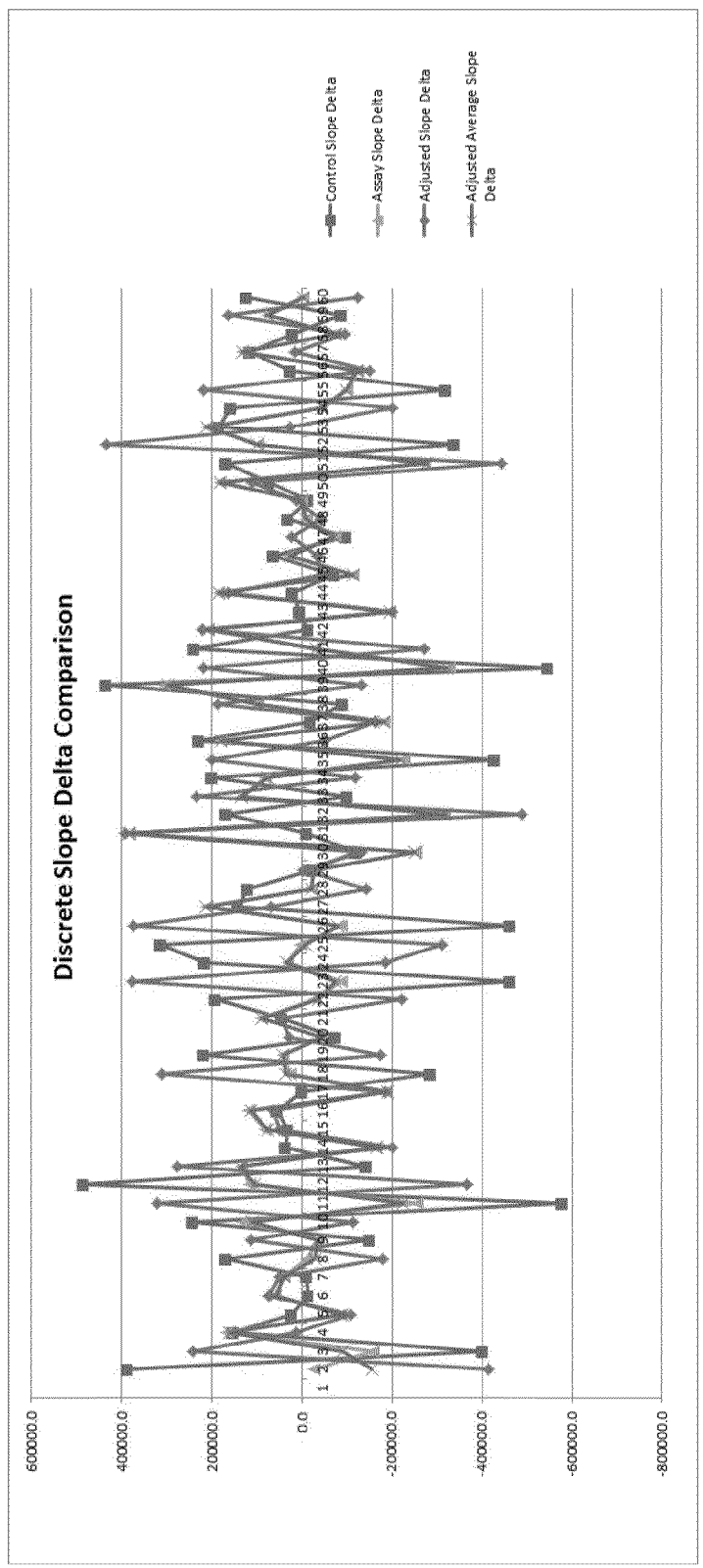

FIG. 28 is a graph of a discrete slope delta comparison according to the detection algorithm of the present invention.

Figure 29:
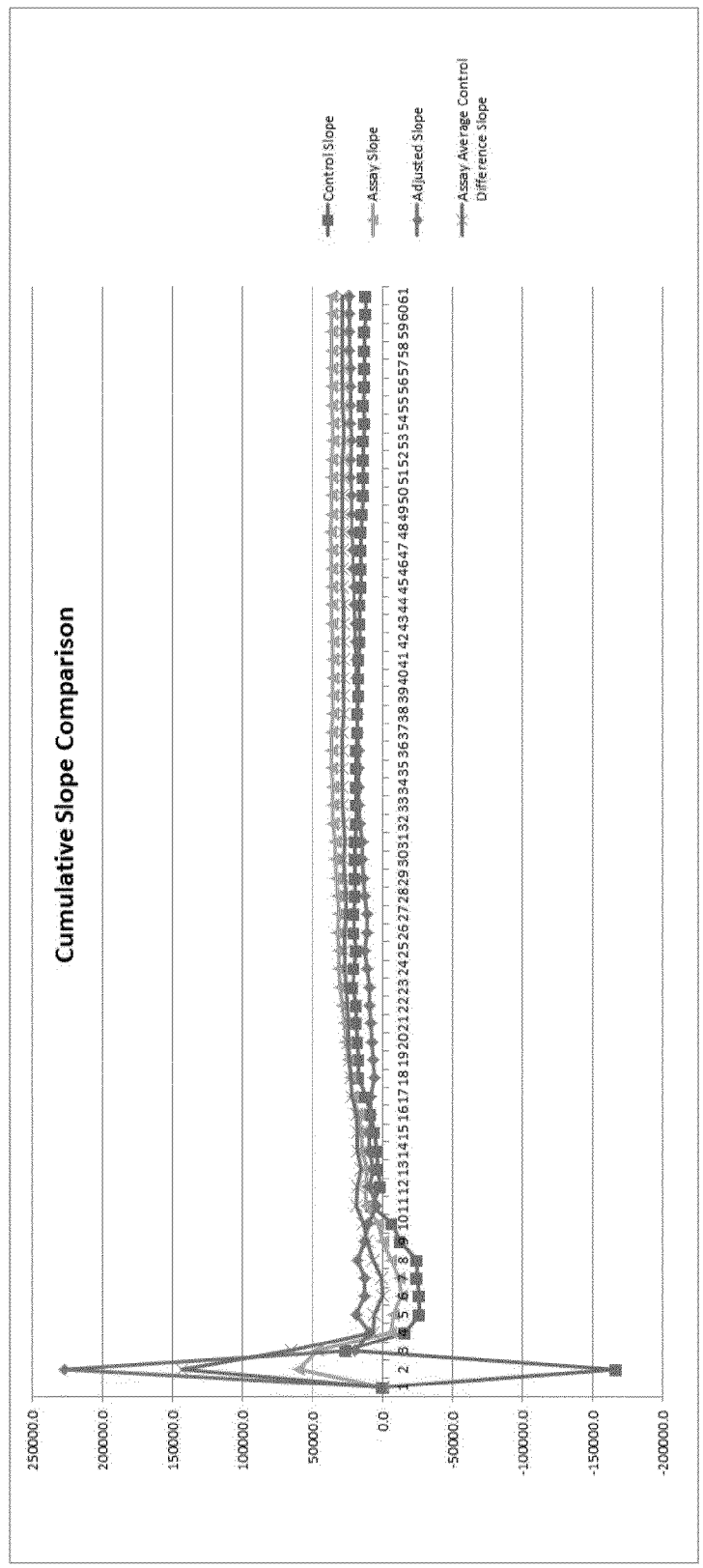

FIG. 29 is a graph of a cumulative slope comparison according to the detection algorithm of the present invention.

Figure 30:
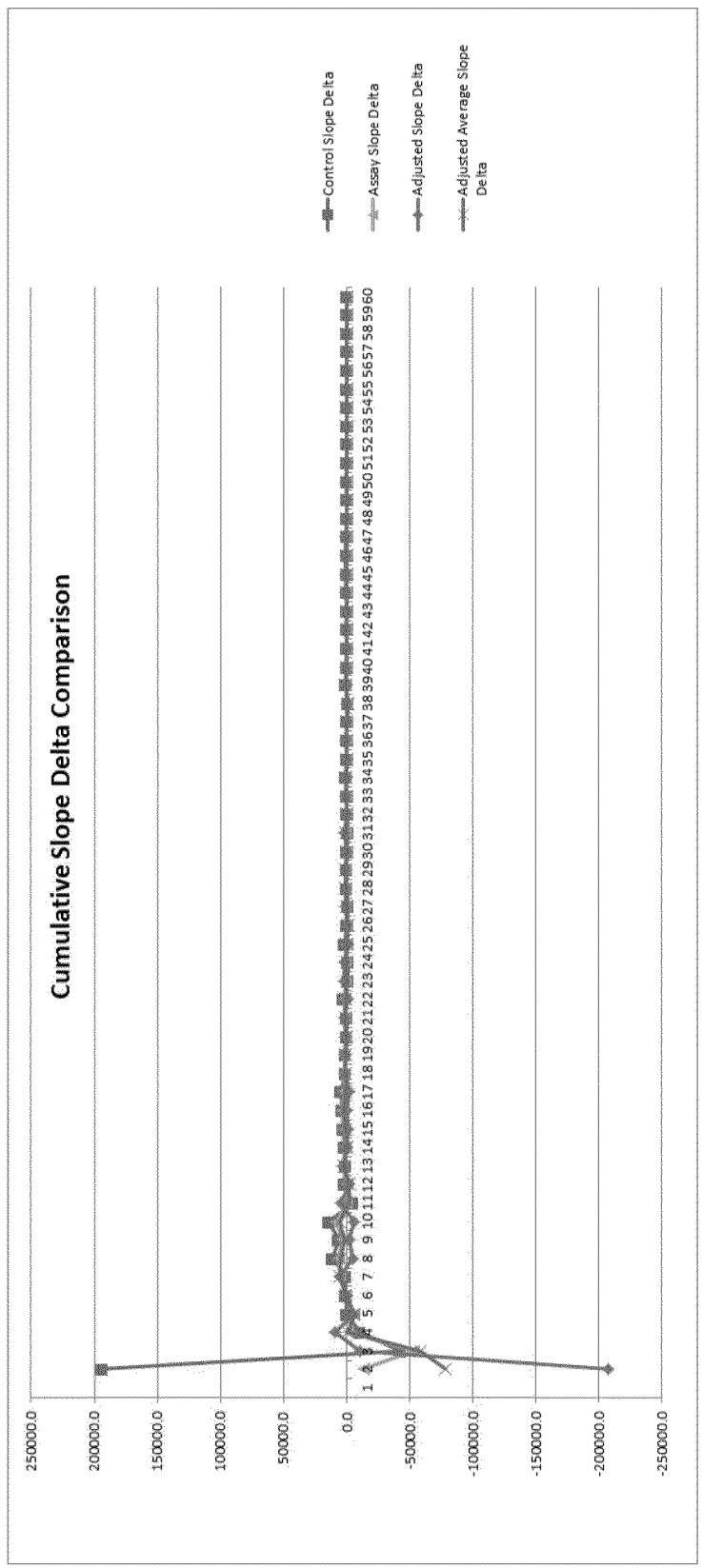

FIG. 30 is a graph of a cumulative slope delta comparison according to the detection algorithm of the present invention.

Figure 31:
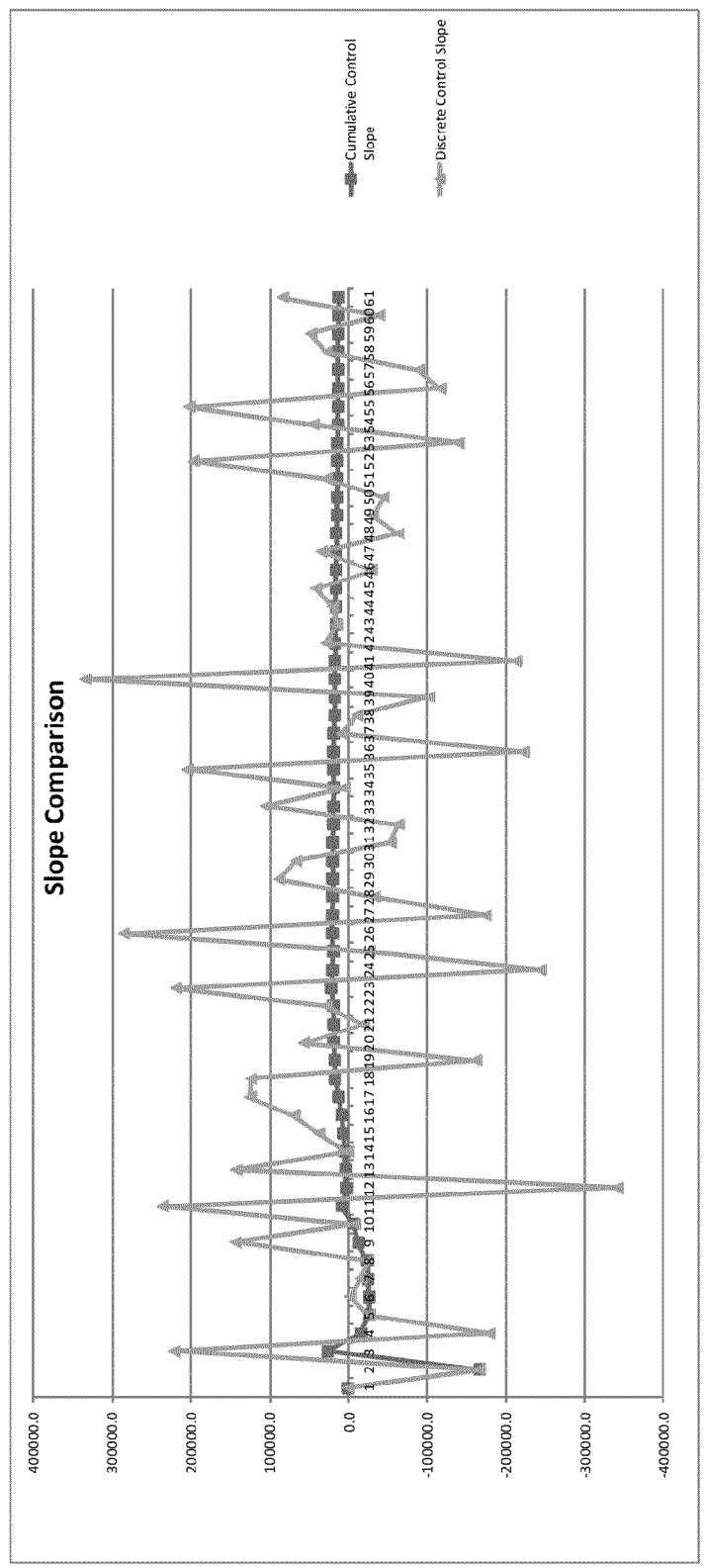

FIG. 31 is a graph of a slope comparison according to the detection algorithm of the present invention.

Figure 32:
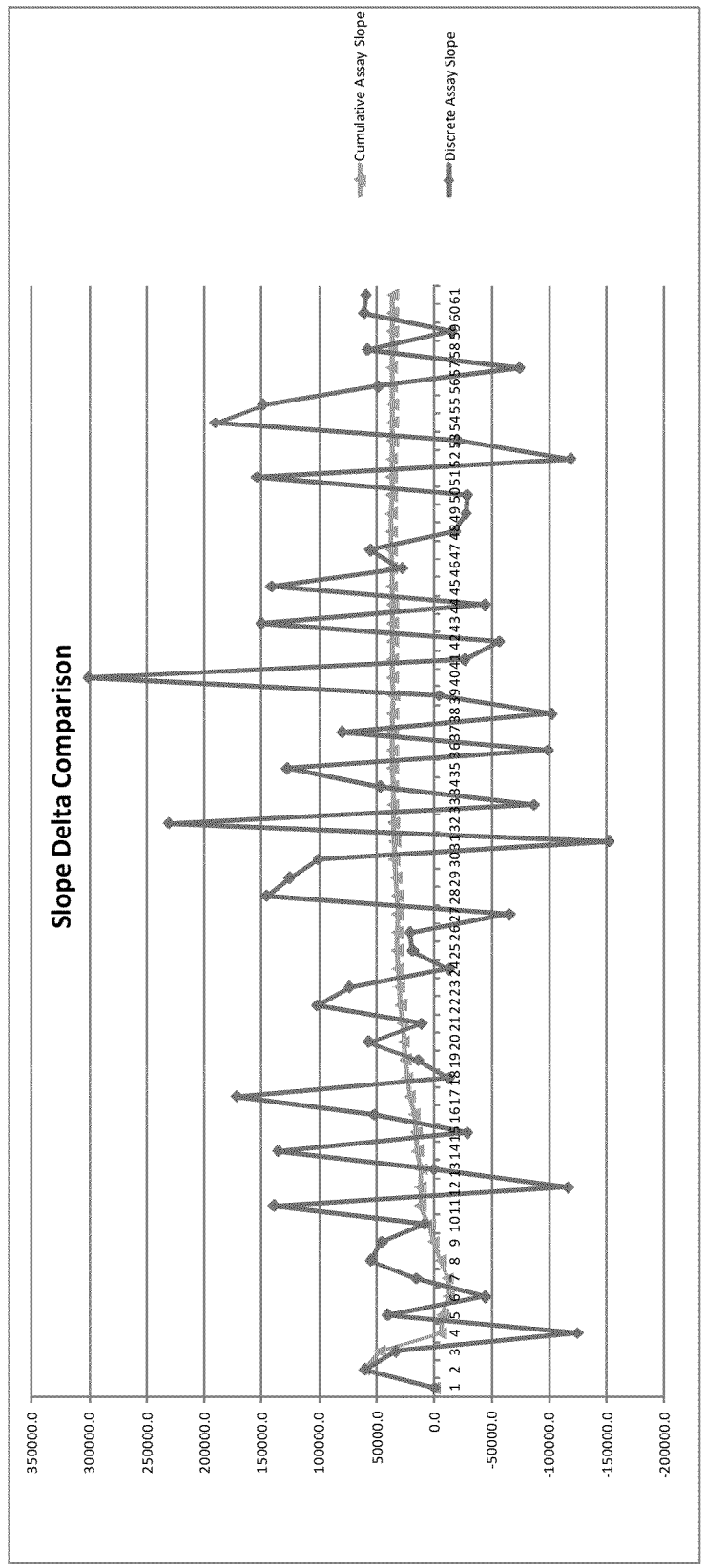

FIG. 32 is a graph of a slope delta comparison according to the detection algorithm of the present invention.

Figure 33:
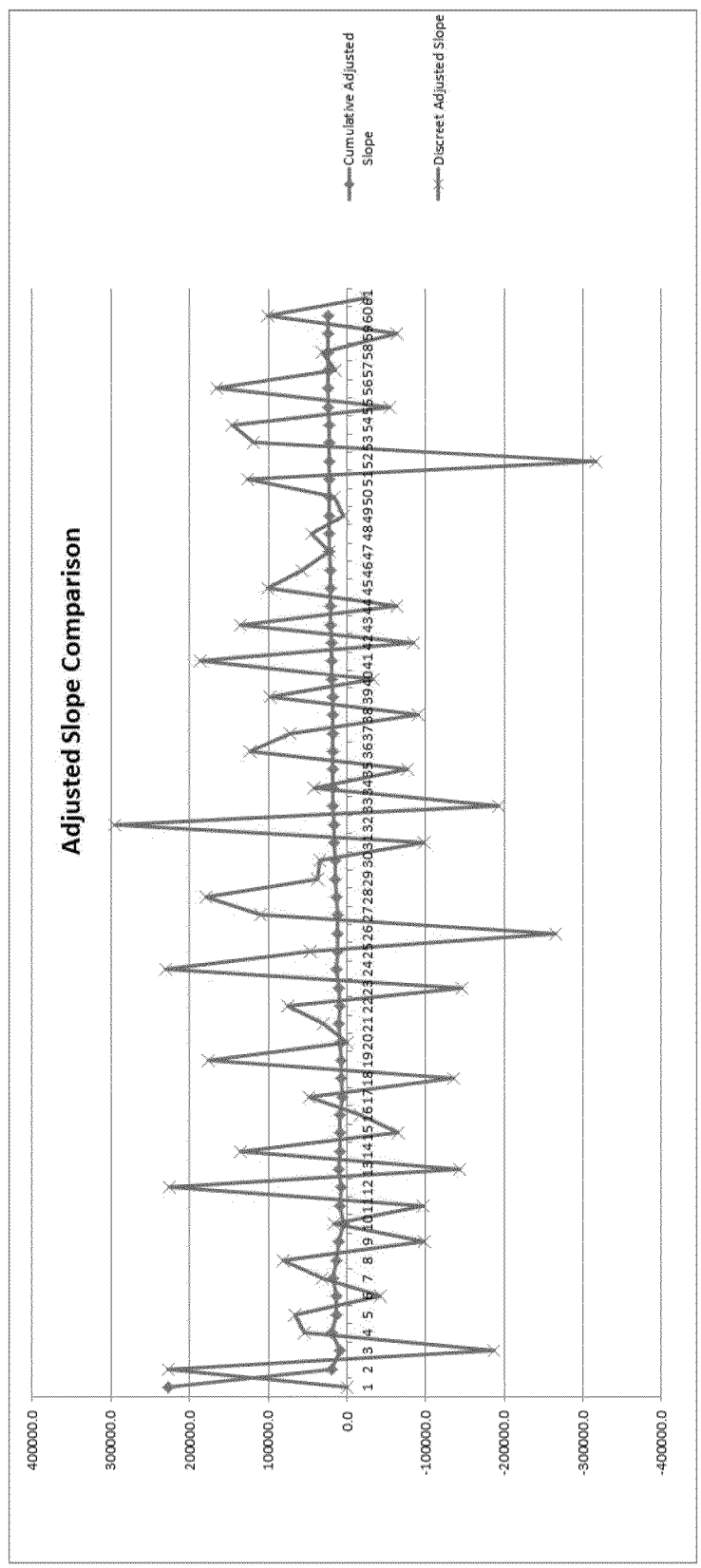

FIG. 33 is a graph of a cumulative and discrete adjusted slope according to the detection algorithm of the present invention.

Figure 34:
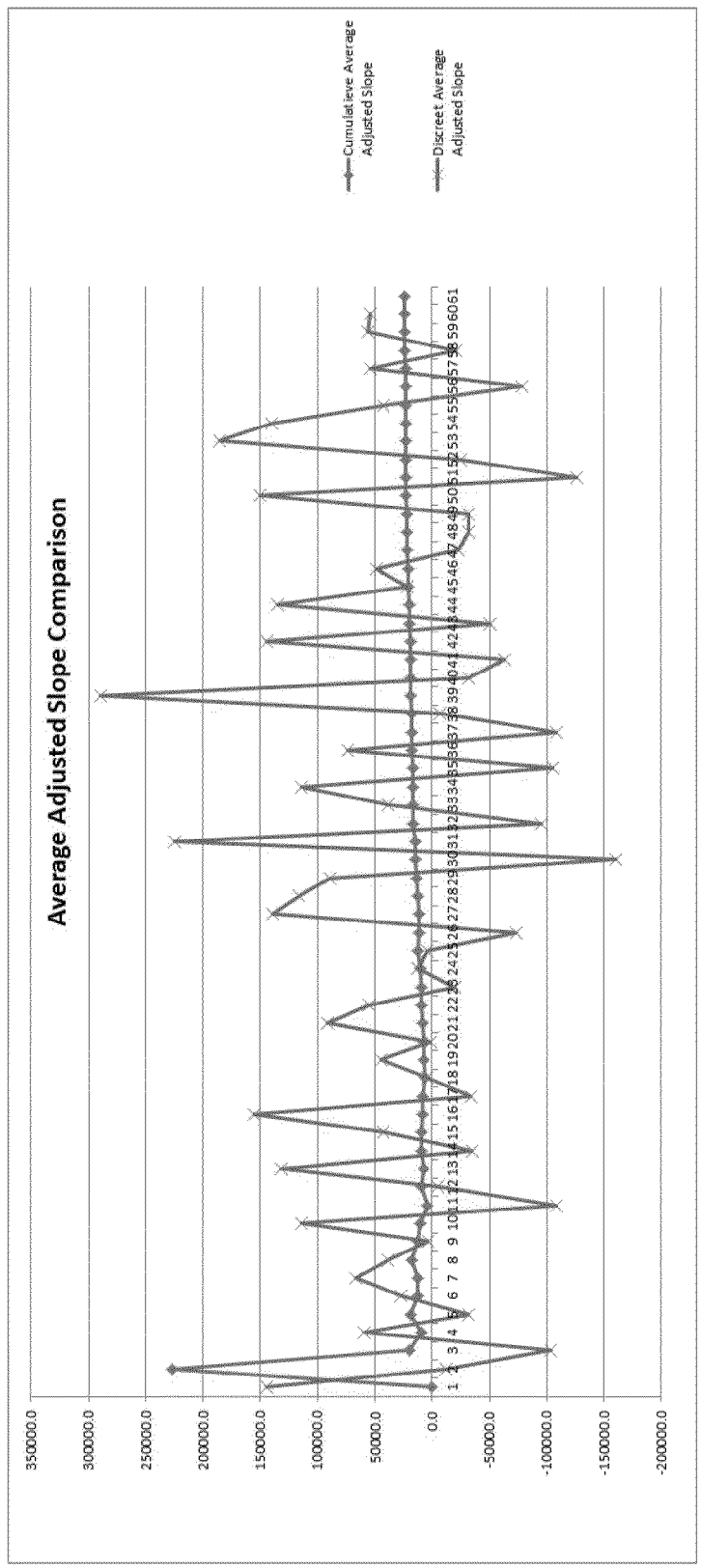

FIG. 34 is a graph of a cumulative and discrete mean adjusted slope according to the detection algorithm of the present invention.

Figure 35:
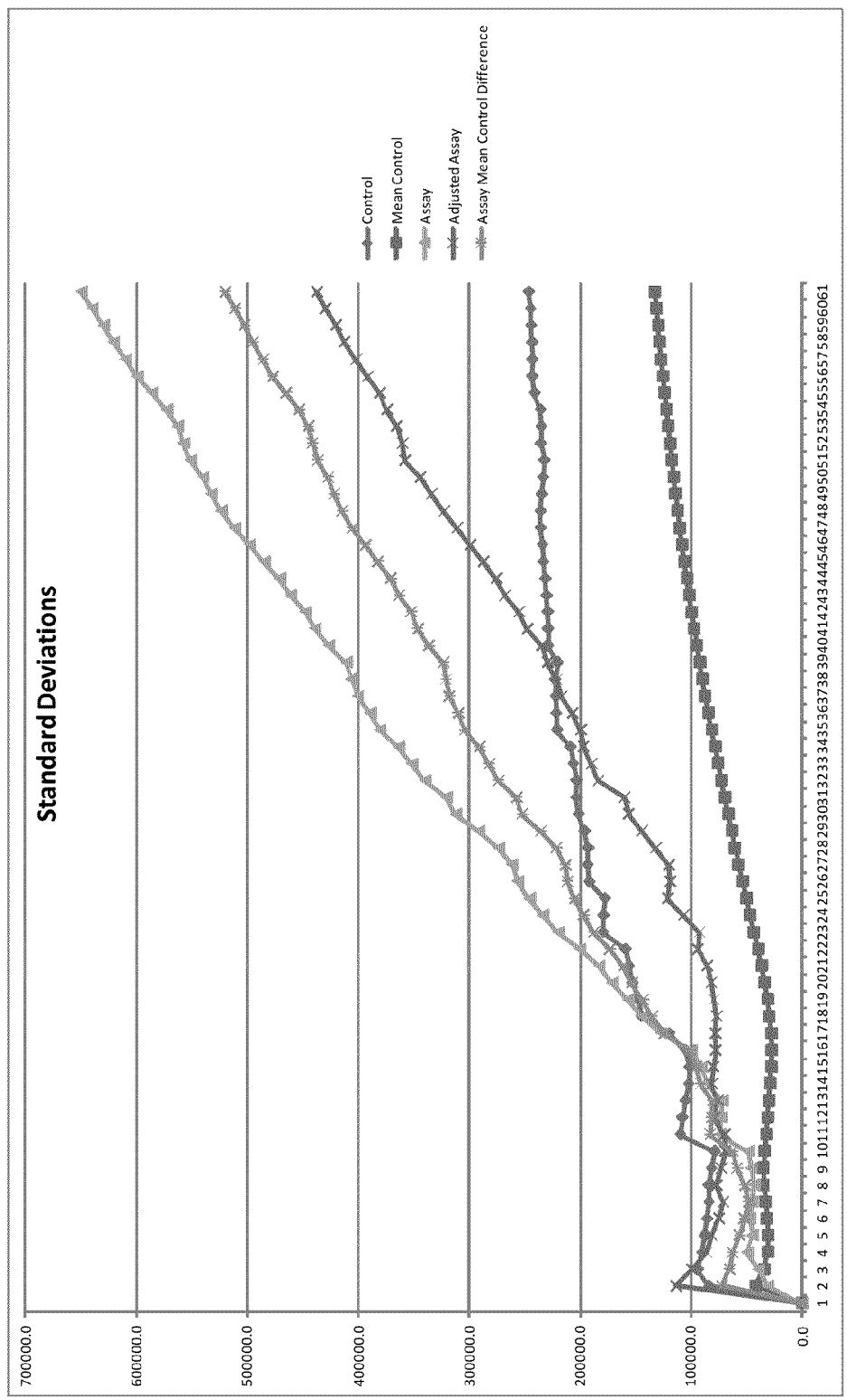

FIG. 35 is a graph of the standard deviations according to the detection algorithm of the present invention.

Figure 36:
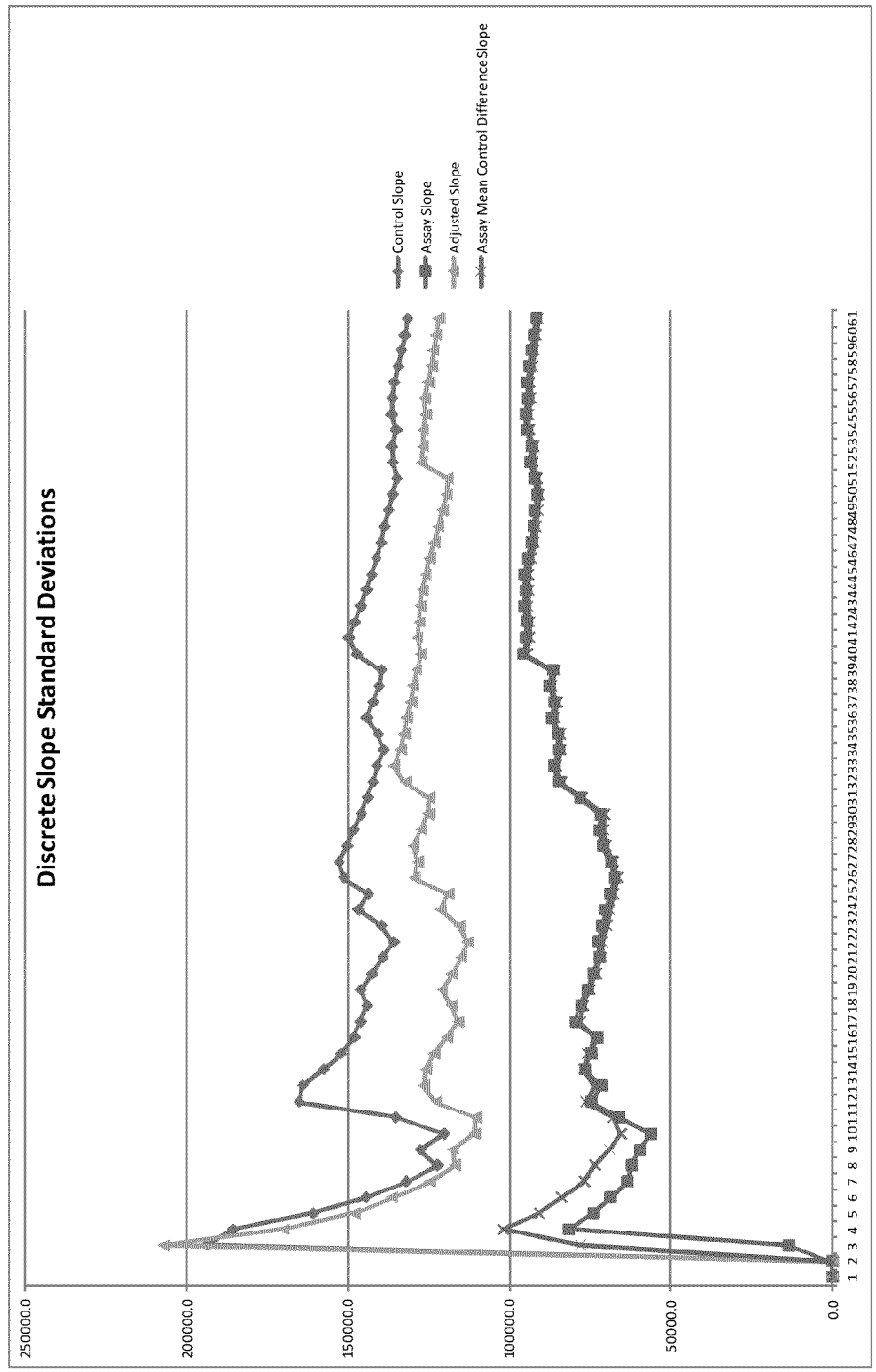

FIG. 36 is a graph of the discrete slope standard deviations according to the detection algorithm of the present invention.

Figure 37:
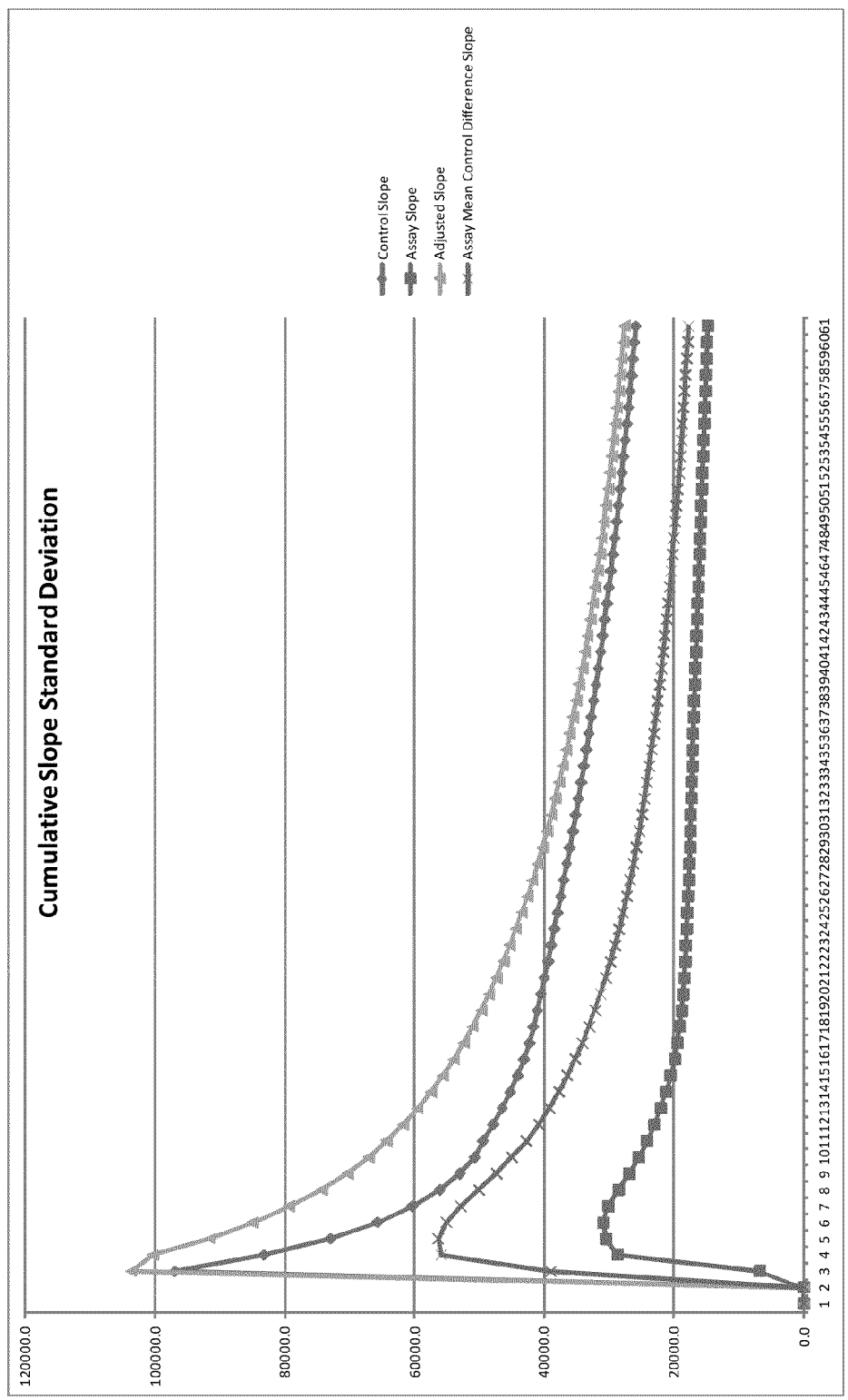

FIG. 37 is a graph of the cumulative slope standard deviations according to the detection algorithm of the present invention.

DETAILED DESCRIPTION OF THE INVENTION

Figure 2:
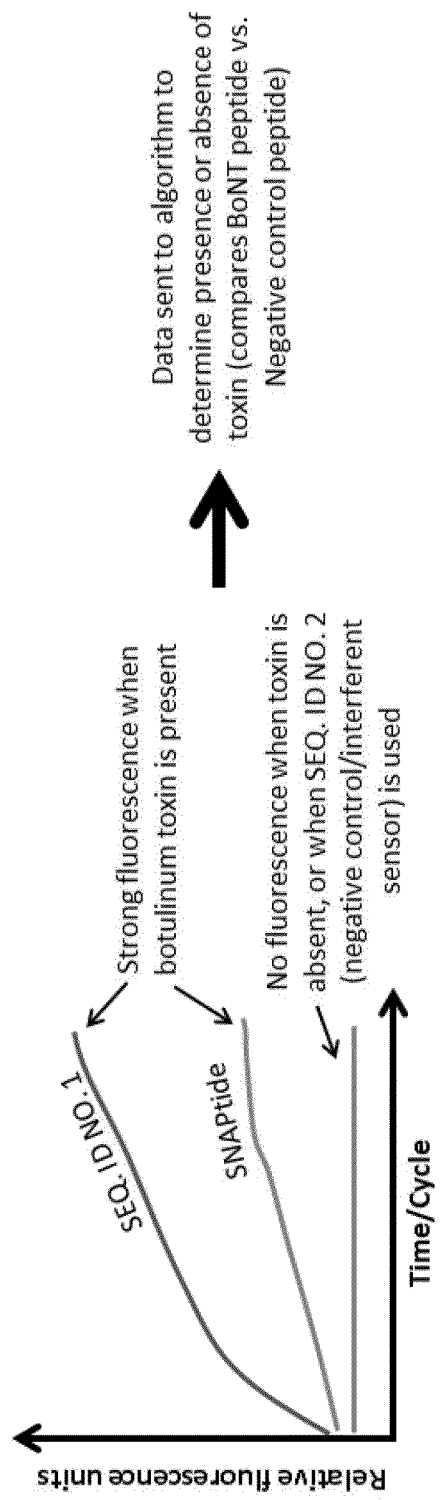
FIG. 2 is a graphical representation of the anticipated fluorescence response and algorithmic data processing of an assay for detecting biologically active botulinum toxin according to the present invention.

Referring now to the drawings, wherein like reference numerals refer to like parts throughout, there is seen in FIG. 1 a schematic of a functional protein assay with BoNT/A according to the present invention, where a fluorescently labeled peptide substrate, comprising a peptide substrate labeled with a fluorophore and a quencher, such as the FITC/DABCYL labeled proof-of principle substrate SNAPtide® or SEQ. ID NO. 1 (Table 1), is contacted by a sample containing botulinum neurotoxin (BoNT/A). For example, SNAPtide® and SEQ. ID NO. 1 have an N-terminal FITC or internal FAM (fluorophore) tag and a C-terminal DABCYL (quencher) tag. Upon cleavage by BoNT/A-LC, the fluorophore and quencher become spatially separated, resulting in increased fluorescence. The results may be monitored by an appropriate temperature controlled fluorescence reader, such as a Rotor-Gene® Q (available from Qiagen, Valencia, Calif.), a FilterMax® F5, a Genedrive®, or a RAZOR® EX system. As seen in FIG. 2, the increase of fluorescence over time may be measured, graphically displayed, and/or compared to a negative control sample using an algorithm to indicate whether biologically active botulinum toxin is present in a given sample.

EXAMPLE 1

Materials

The assay according to the present invention was initially developed using recombinant Botulinum Neurotoxin Type A Light Chain (BoNT/A-LC) from List Biological Laboratories, Inc. (Campbell, Calif.) and later confirmed using Botulinum Neurotoxin Type A complex from BEI Resources (Manassas, Va.). Botulinum Type A Complex Toxoid (BoNT/A Complex inactivated by formalin) from Metabiologics, Inc (Madison, Wis.) along with heat-inactivated BoNT/A-LC (boiled for 30 min) were used to confirm the specificity of the assay to BoNT/A activity in the studies. Studies were performed using SNAPtide®, a peptide substrate labeled with the FITC/DABCYL FRET pair, purchased from List Biological Laboratories, Inc. (Campbell, Calif.). Later studies were performed using designed and synthesized fluorescent peptide substrates (SEQ. ID NOS. 1 through 6) with the FAM/DABCYL FRET pair (Table 1). Hepes buffer solution and tris(2-carboxyethyl)phosphine (TCEP) were purchased from Sigma-Aldrich (Saint Louis, Mo.). Dithiothreitol (DTT), Triton X-100, zinc chloride ($ZnCl_2$), Tween® 20, Phosphate Buffered Saline (PBS) solution, and Bovine serum albumin (BSA) were purchased from Fisher Scientific (Waltham, Mass.).

TABLE 1

Synthesized fluorescent peptide substrates

| | |
|---|---|
| SEQ. ID NO. 1 | MDENLEQVSGIIGNLRHMALDMGNEIDTQNRQIDRIMEKAD<br>SN(KDabcyl)TRIDEANQRATKML(K5Fam) |
| SEQ. ID NO. 2 | MDENLEQVSGIIGNLRHMALDMGNEIDTQNRQIDRIMEKAD<br>SN(KDabcyl)TREDIQATNRAKML(K5Fam) |
| SEQ. ID NO. 3 | MDENLEQVSGIIGNLRHMALDMGNEIDTQNRQIDRIMEKAD<br>SN(KDabcyl)TREDIQNARTAKML(K5Fam) |
| SEQ. ID NO. 4 | MDENLEQVSGIIGNLRHMALDMGNEIDTQNRQIDRIMEKAD<br>SN(KDabcyl)TREDIQNATARKML(K5Fam) |
| SEQ. ID NO. 5 | MDENLEQVSGIIGNLRHMALDMGNEIDTQNRQIDRIMEKAD<br>SN(KDabcyl)TREDIQNATRAKML(K5Fam) |
| SEQ. ID NO. 6 | (KDabcyl)TRIDEANQRATKML(K5Fam) | where (KDabcyl) = Lys labeling by Dabcyl (or other quencher), (K5Fam) = Lys labeling by 5-Carboxyfluorescein (or other fluorophore), and QR = BoNT/A cleavage site Common PCR Inhibitors Arizona road dust was purchased from Powder Technology, Inc. (Burnsville, Minn.). Arizona road dust was collected on a SASS® 3100 filter cartridge; from Research International (Monroe, Wash.), and extracted into 1×PBS containing 0.05% (v/v) Triton X-100 using the SASS® 3100 Dry Air Sampler and SASS® 3010 Particle Extractor systems from Research International. The extracted Arizona road dust was centrifuge for 5 minutes at 5000 rpm in an Eppendorf table top centrifuge, and the supernatant was used for inhibition studies. Arizona road dust was also utilized for protease activity studies, where a 100 mg/mL Arizona road dust mixture was made in $H_2O$, vortexed for 1 minute, then allowed to settle for 30 minutes. The resulting supernatant was collected for use in the fluorescent peptide substrate based protease activity experiments.

Diesel exhaust residue from a tractor was collected onto a SASS® 3100 filter cartridge. The filter containing the exhaust residue was extracted with 1×PBS containing 0.05% (v/v) Triton X-100 using the SASS® 3010 Particle Extractor system. The resulting solution was used directly in inhibition studies.

Humic acid was purchased from Fisher Scientific (Waltham, Mass.), and was dissolved in 1×PBS containing 0.05% (v/v) Triton X-100 for use in subsequent inhibition studies.

BoNT/A Assay Development and Optimization in the Rotor-Gene® Q Using SNAPtide®

Initial experiments tested a series of three SNAPtide® concentrations (5, 10, and 20 µM) and 6 amounts of BoNT/A-LC (0.28, 1.4, 2.8, 7.14, 14.3, and 28.6 ng) in the following assay buffer: 50 mM Hepes buffer pH 7.4+0.05% (v/v) Tween® 20. Reactions were incubated in the Rotor-Gene® Q real-time PCR cycler using the following cycling profile: 60×1 minute cycles at 37° C. The Rotor-Gene® Q acquired a fluorescence signal at the end of each cycle and was able to detect BoNT/A-LC activity in real-time. A 10 µM SNAPtide® was chosen as the optimal peptide substrate concentration for the assay. Initial experiments in the Rotor-Gene® Q were performed using 60×1 minute cycles, but later were adjusted to 55×1 minute cycles to match the RAZOR® EX settings.

Next, different assay buffers were tested using the 10 µM SNAPtide® concentration and 3 amounts of BoNT/A-LC. The following buffers were compared: 50 mM Hepes buffer pH 7.4+0.05% (v/v) Tween® 20, 50 mM Hepes buffer pH 7.4+1 mg/mL BSA, 34.5 mM Hepes buffer pH 7.4+0.03% Tween 20+0.31% PBS+0.02% (v/v) Triton X-100, and 34.5 mM Hepes buffer pH 7.4+0.69 mg/mL BSA+0.31% PBS+ 0.02% (v/v) Triton X-100 (FIG. 1). PBS+Triton X100 is commonly used to extract agents, such as BoNT/A, from collected environmental samples. The assay was optimized for working with 0.31% PBS and 0.02% (v/v) Triton X-100. Tween® 20 and BSA are commonly added to enhance protein stability during analysis. However, BSA caused negative controls containing 10 µM SNAPtide® and no BoNT/A-LC to fluoresce, so the use of Tween® 20 was preferred. As seen in FIG. 3, assays were incubated at 37° C. for 55 cycles (1 cycle/minute) with fluorescence acquisition at the end of each cycle. BSA caused the negative controls to fluoresce, so the optimal assay buffer chosen was 34.5 mM Hepes buffer pH 7.4+0.03% Tween® 20+0.31% PBS+0.02% Triton X-100. Thus, the Example moved forward using 34.5 mM Hepes buffer pH 7.4+0.03% (v/v) Tween® 20+0.31% PBS+0.02% (v/v) Triton X-100 as the assay buffer.

Finally, the assay was optimized in the Rotor-Gene® Q to work with the full length BoNT/A protein by testing different concentrations of $ZnCl_2$ and DTT. The use of a reducing agent, such as DTT, is required to detect BoNT/A as the BoNT/A-LC and HC disulfide bonds needs to be broken to allow for BoNT/A-LC mediate peptide cleavage. The addition of $ZnCl_2$ to the assay mix with DTT is necessary as DTT can chelate zinc, which is required for BoNT/A-LC protease activity. As seen in FIG. 4, the activity of 1.9 ng and 7.5 ng BoNT/A-LC using varying concentrations of $ZnCl_2$ and DTT was tested. The addition of DTT alone reduced BoNT/A-LC activity and 0.3 mM $ZnCl_2$ was found to be the optimal concentration of $ZnCl_2$ required to counteract this reduction in activity (data not shown). Addition of the common PCR inhibitors humic acid (0.16 μg/mL) and diesel exhaust residue (1:10 dilution) did not affect the activity of BoNT/A-LC in the presence of various DTT concentrations and 0.3 mM $ZnCl_2$. In these experiments, 10 μM SNAPtide® and the following assay buffer were used: 34.5 mM Hepes buffer pH 7.4+0.03% (v/v) Tween® 20+0.31% PBS+0.02% (v/v) Triton X-100.

BoNT/A Assay Development and Optimization in the RAZOR® EX Using SNAPtide®

The experiments performed in the Rotor-Gene® Q were translated to the RAZOR® EX. An initial experiment was performed in the RAZOR® EX using a configuration profile created specifically for this assay. This configuration profile used the following cycling parameters: 55×1 minute cycles at 37° C. while acquiring fluorescence at the end of each cycle. Referring to FIG. 5, a range of BoNT/A-LC amounts (0.11 ng-30 ng) was tested using 10 μM SNAPtide® and 50 mM Hepes pH 7.4+0.05% (v/v) Tween® 20 assay buffer. The RAZOR® EX was able to detect BoNT/A-LC activity in real-time. The ability of the RAZOR EX® was then tested to detect BoNT/A-LC activity using the 34.5 mM Hepes buffer pH 7.4+0.03% (v/v) Tween® 20+0.31% PBS+0.02% (v/v) Triton X-100 buffer. As seen in FIG. 6, a range of BoNT/A-LC (0.06 ng-7.5 ng)+10 μM SNAPtide® was assayed using 34.5 mM Hepes buffer pH 7.4+0.03% (v/v) Tween 20+0.31% PBS+0.02% (v/v) Triton X-100 buffer. The RAZOR® EX was able to detect BoNT/A-LC activity in real-time.

In order to optimize the $ZnCl_2$ and DTT concentrations for use in the RAZOR® EX, the assay buffer was altered to 32.2 mM Hepes buffer pH 7.4+0.03% Tween 20+0.30% PBS+ 0.02% Triton X-100, and used 9.64 μM SNAPtide®. Referring to FIG. 7, the combination of 2.5 mM DTT and 0.3 mM ZnC12 was compatible, as the addition of DTT is required to detect the full length BoNT/A protein.

The 2.5 mM DTT and 0.3 mM $ZnCl_2$ conditions were chosen as optimal concentrations and therefore utilized to test the performance of the assay in the RAZOR® EX in the presence of common PCR inhibitors, as seen in FIGS. 8-10. As seen in FIG. 8, 1.9 ng-7.5 ng BoNT/A-LC in the presence of diesel exhaust residue established that diesel exhaust residue did not inhibit BoNT/A-LC activity. As seen in FIG. 9, 0.04 mg/mL-0.08 mg/mL of Arizona road dust did not inhibit 7.5 ng BoNT/A-LC. Finally, as seen in FIG. 10, 7.5 ng BoNT/A-LC established that the BoNT/A-LC assay is compatible with humic acid concentrations up to 0.23 μg/mL.

Design of SEQ. ID NO. 1 and SEQ. ID NO. 2 BoNT/A Fluorescent Peptide Substrates

Based on the studies utilizing SNAPtide® in the Rotor-Gene® Q and the RAZOR® EX, the detection of biologically active BoNT/A-LC protein toxin was shown to be possible on a qPCR platform given the correct buffer conditions and PCR parameters. While SNAPtide® is a good candidate for BoNT/A-LC activity, it did have issues with stability, solubility, and detection signal. The instability of the SNAPtide® peptide was shown in a number of experiments where the negative control samples showed large and unexpected increases in fluorescence, followed by drops in fluorescence signal overtime. Additionally, solubility issues were identified in some of our solutions where precipitation of SNAPtide® was observed in both stock samples and experimental samples. Finally, the detection signal of SNAPtide® was not ideal as a large amount of BoNT-A LC is required in order to generate a high enough signal over noise to allow detection of BoNT-A LC activity based on an algorithmic determination. Therefore, a new BoNT-A peptide substrate design was utilized.

Figure 11A:
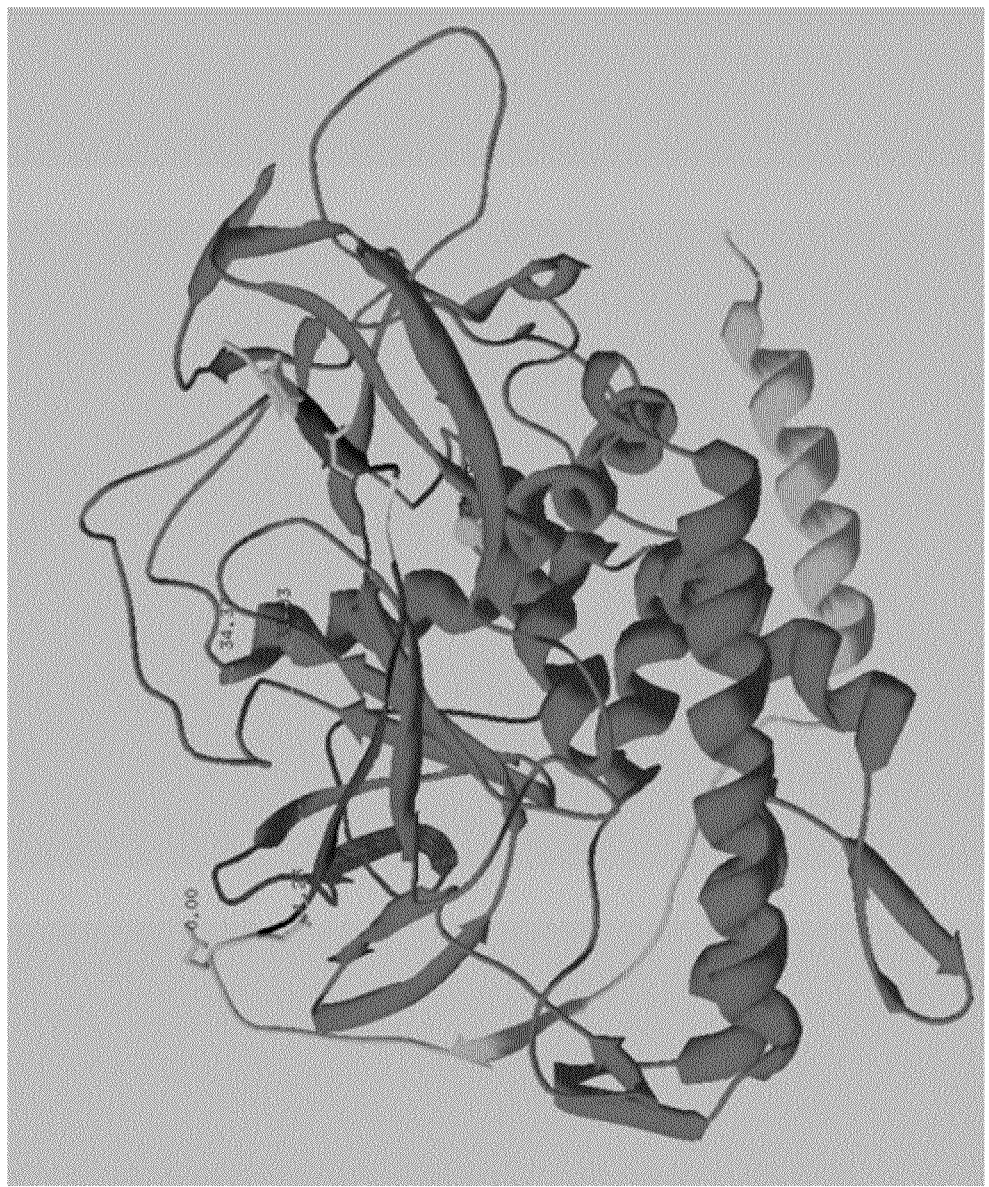
Figure 11B:
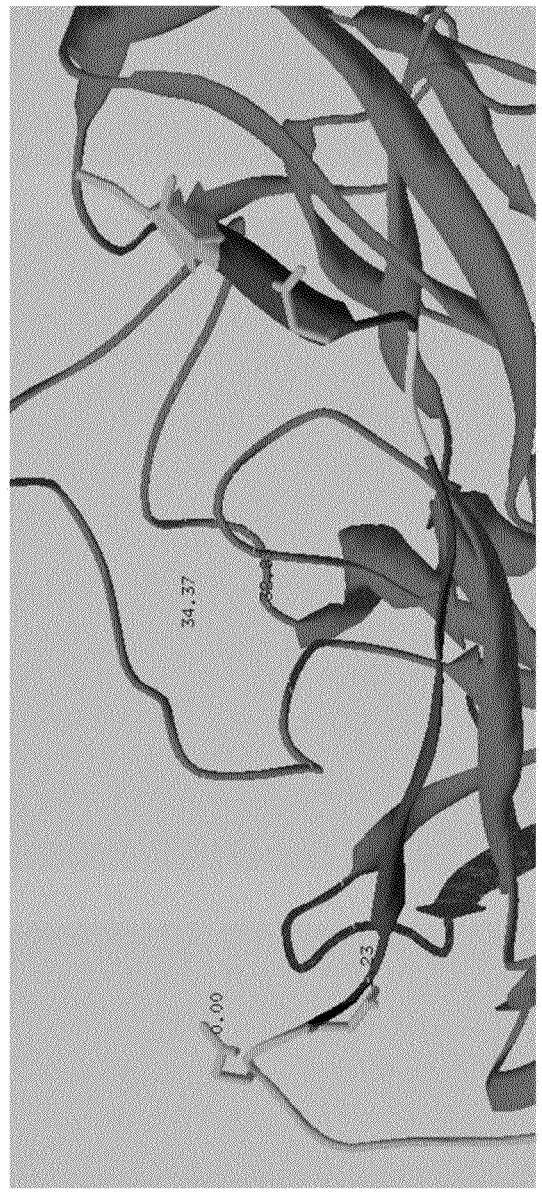
Figure 11C:
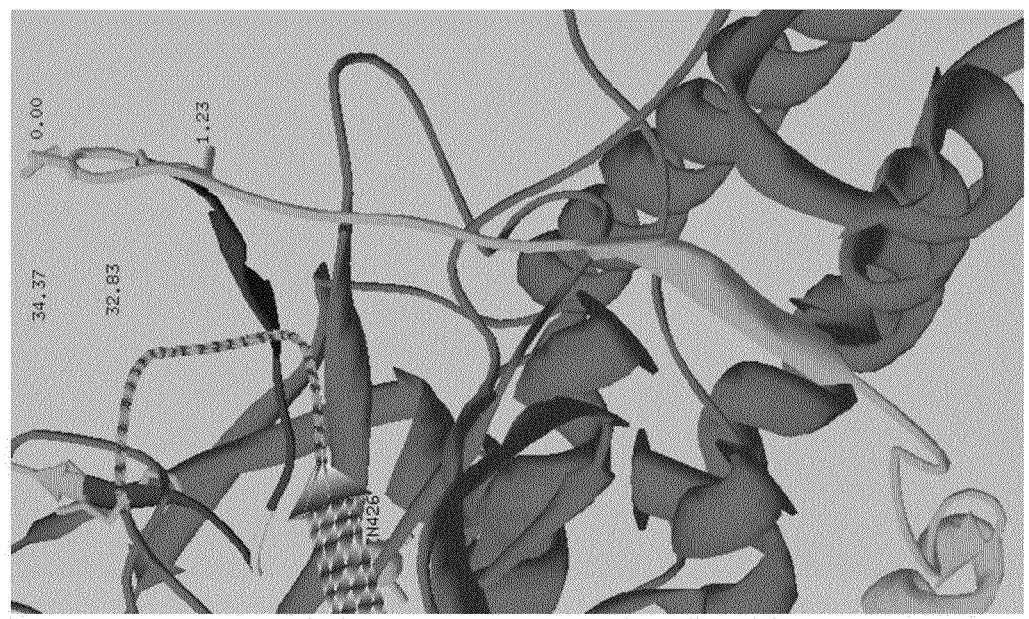
Figure 11D:
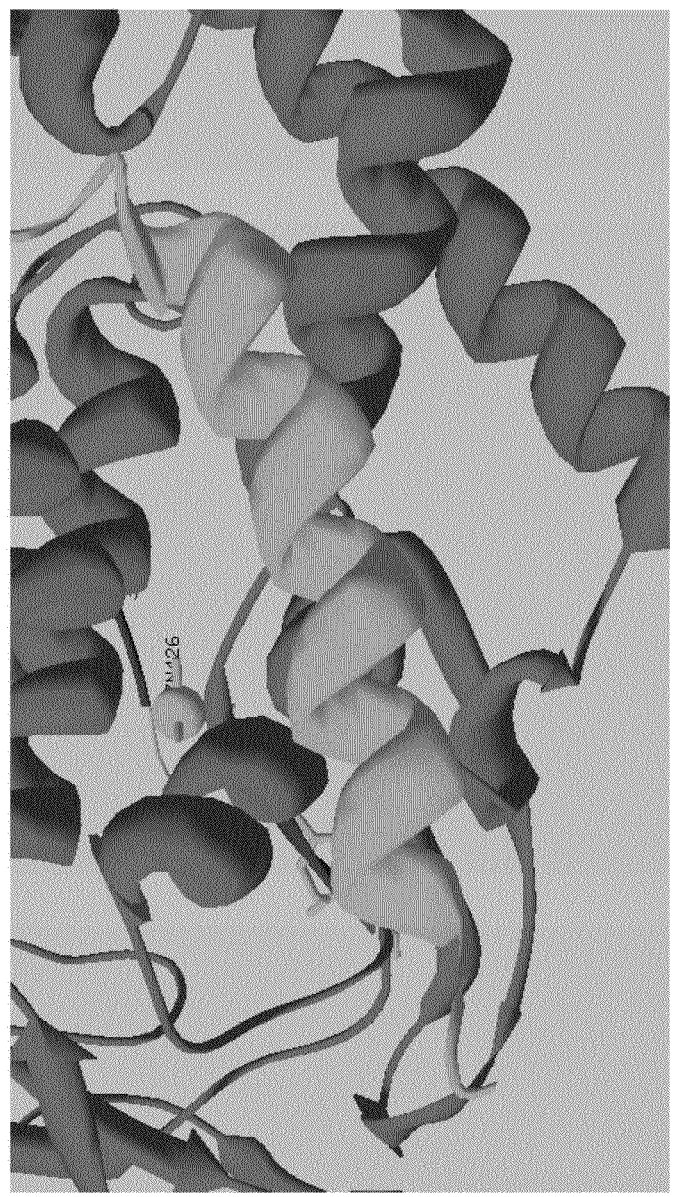

The present invention includes six fluorescent peptide substrates for BoNT/A detection (Table 1). The SNAPtide® peptide substrate is known to only include a short SEQ. ID NO. (about 15 amino acids in length) resembling the BoNT/A cleavage site on SNAP-25. While BoNT/A can cleave the SNAPtide® peptide substrate, BoNT/A binding to SNAPtide® is not ideal due to the exclusion of BoNT/A binding domains found on SNAP-25. Therefore, to increase the binding efficiency of BoNT/A, a 59 amino acid fluorescent peptide (SEQ. ID NO. 1) based on the SNAP-25/BoNT/A interaction was designed. Shown in the three-dimensional Swiss PDB viewer representations in FIG. 11, BoNT/A-LC (in red) interacts with the C-terminal portion (Green/Blue) of the SNAP-25 protein. The BoNT/A cleavage area (dark blue) and cleavage site (light blue) on SNAP-25 fall within a pocket within BoNT/A-LC protease (FIG. 11A-B). Due to the acceptable distance (32.8 Angstroms) between the lysines located on the peptide SEQ. ID NO. (FIG. 11B), these residues were chosen as the location of fluorophore and quencher for the FRET pair. While the internal region of the peptide was not shown to have any obvious interactions with the BoNT/A-LC (FIG. 11C), an alpha-helical structure located in a SNARE region of the SNAP-25 did interact with BoNT/A-LC (FIG. 11D). Based on these observations, the SEQ. ID NO. 1 fluorescent peptide was designed (Table 1).

To design a negative control fluorescent peptide, it had to meet two criteria: 1) Cannot be cleaved to BoNT/A-LC and 2) Must be sensitive to any interferents that affect the SEQ. ID NO. 1 peptide. Based on these criteria, four potential negative control fluorescent peptides were designed (SEQ. ID NOS. 2-5; Table 1). In each of the peptides, the fluor/quencher region was mutated in such a way to destroy the BoNT/A recognition/cleavage site. These SEQ. ID NO. s were then run through the ExPASy cleavage predictor software to determine if the fluor/quencher regions still possessed similar cleavage maps based on the known proteases (FIG. 12). While SEQ. ID NO. 1 can be cleaved by 16 different proteases in 36 different potential cleavages, SEQ. ID NO. 2 was shown to be cleaved by the same number of proteases in the same number of cleavages (FIG. 12A). Additionally, the SEQ. ID NO. 2 fluor/quencher contained an 8 amino acid difference in the peptides BoNT/A cleavage recognition site compared to SEQ. ID NO. 1 (Table 1). Therefore, the SEQ. ID NO. 2 negative control/interferents sensing peptide was chosen over the other negative controls due to various reasons as listed in the FIGS. 12B-C.

BoNT/A Assay Development and Optimization in the FilterMax® F5 Using SEQ. ID NO. 1

Initial experiments with SEQ. ID NO. 1 were performed to determine its capability in detecting BoNT/A-LC activity compared to the proof-of-principle peptide SNAPtide®. The FilterMax® F5 fluorimeter was used in this testing because it possesses a heat controlled sample detection area (can be regulated from 25 to 45° C.) and can precisely detect changes in fluorescence of a broad detection range over a time course. Similar concentrations of SEQ. ID NO. 1 and SNAPtide® (10 μM) were used to detect 3 different amounts of BoNT/A-LC (7.5, 15, and 30 ng) in a 96 well plate (100 μL per well). Similar buffer conditions (30 mM Hepes pH 7.4, 0.2% Tween 20), that were optimized from the proof-of-principle studies, were used for all the samples in the assay. The reactions were incubated at 37° C. for 60 minutes, with fluorescence readings taken at 1 minute intervals. As seen in FIG. 13, a greater increase in fluorescence overtime was observed in all SEQ. ID NO. 1 samples compare to SNAPtide® samples at all BoNT/A-LC conditions tested. These results show that the SEQ. ID NO. 1 fluorescence substrate produces a greater signal than that of SNAPtide®. Additionally, based on observational studies SEQ. ID NO. 1 is more stable (does not precipitate) and produces very little fluorescence background noise compared to SNAPtide®.

Importance of the BoNT/A Binding Region in SEQ. ID NO. 1 Compared to SEQ. ID NO. 6

As SEQ. ID NO. 1 was designed to possess an alpha-helical binding region to enhance its interaction with BoNT/A (FIG. 11D), the next test was designed to assess the importance of this region in detection BoNT/A activity. SEQ. ID NO. 6 was designed to lack the BoNT/A binding region that is found in SEQ. ID NO. 1 (Table 1). Similar concentrations of SEQ. ID NO. 1 and SEQ. ID NO. 6 (10 μM) were used to detect 2 different amounts of BoNT/A-LC (15 and 30 ng) in a 96 well plate (100 μL per well; 30 mM Hepes pH 7.4, 0.2% Tween 20) to be analyzed on the FilterMax® F5 fluorimeter. The reactions were incubated at 37° C. for 60 minutes, with fluorescence readings taken at 1 minute intervals. As seen in FIG. 14, while SEQ. ID NO. 1 was able to detect BoNT/A-LC, the lack of the BoNT/A binding region on SEQ. ID NO. 6 rendered it incapable of detecting BoNT/A-LC activity.

SEQ. ID NO. 1 Detects Biologically Active BoNT/A, but not Heat or Formalin Inactivated BoNT/A The present invention was designed to produce an assay capable of detecting only the biologically active form of BoNT/A. Therefore, versions of BoNT/A that were known to be inactivated either through heating (heat inactivated BoNT/A-LC) or through chemical treatment with formalin (BoNT/A Toxoid) were assessed in our studies with SEQ. ID NO. 1. Due to the high signal produced using SEQ. ID NO. 1, we were able to optimize our conditions to only use 1 μM instead of 10 μM SEQ. ID NO. 1 (data not shown). SEQ. ID NO. 1 (1 μM) was used in a detection assay with BoNT/A-LC (1 and 5 ng), heat inactivated BoNT/A-LC (5 and 80 ng), and BoNT/A Toxoid (20 and 200 ng) in a 96 well plate (100 μL per well; 30 mM Hepes pH 7.4, 0.2% Tween 20) to be analyzed on the FilterMax® F5 fluorimeter. The reactions were incubated at 37° C. for 60 minutes, with fluorescence readings taken at 1 minute intervals. As seen in FIG. 15A, SEQ. ID NO. 1 was able to detection biologically active BoNT/A-LC (5 ng), but not heat inactivated BoNT/A-LC, even when present at high concentrations. Similarly, as seen in FIG. 15B, SEQ. ID NO. 1 was able to detect biologically active BoNT/A-LC (1 ng), but not BoNT/A Toxoid, even when present at high concentrations. Therefore, assays utilizing SEQ. ID NO. 1 can differentiate between biologically active and biologically inactive BoNT/A.

Development of SEQ. ID NO. 2 as a Negative Control/Interferent Sensor for the BoNT/A Assay The present invention was designed to produce a BoNT/A detection assay capable of producing a signal that can be inputted into an algorithm to determine if a sample possesses or lacks biologically active BoNT/A. In order to make this determination, the algorithm not only needs a signal from an input that can detect the presence or absence of BoNT/A, but it also requires a signal that is a negative control, which provides information regarding the background fluorescence in a system. This negative control must be insensitive to BoNT/A mediated cleavage, yet it must be able to register the background noise (interference) present in the system which may affect the detecting substrate (SEQ. ID NO. 1). Therefore, SEQ. ID NO. 2 was designed as this negative control/interference sensor. SEQ. ID NO. 1 and SEQ. ID NO. 2 (1 μM) were used in a detection assay with BoNT/A-LC (5 and 50 ng) in a 96 well plate (100 μL per well; 30 mM Hepes pH 7.4, 0.2% Tween 20) to be analyzed on the FilterMax® F5 fluorimeter. The reactions were incubated at 37° C. for 60 minutes, with fluorescence readings taken at 1 minute intervals. As seen in FIG. 16A, while SEQ. ID NO. 1 was able to detect biologically active BoNT/A-LC (5 and 50 ng), SEQ. ID NO. 2 showed no increase in fluorescence over time in the presence of BoNT/A-LC, even at high concentrations. Therefore, SEQ. ID NO. 2 is capable of acting as a negative control in the BoNT/A detection assay. In a separate test, SEQ. ID NO. 1 and SEQ. ID NO. 2 (1 μM) were used in a detection assay with 100 mg/mL Arizona road dust (ARD), a common PCR inhibitor, with observed protease activity. This assay was performed in a 96 well plate (100 μL per well; 30 mM Hepes pH 7.4, 0.2% Tween 20) and analyzed on the FilterMax® F5 fluorimeter at 37° C. for 60 minutes, with fluorescence readings taken at 1 minute intervals. As seen in FIG. 16B, ARD non-specifically caused an increase in fluorescence (due to the presence of proteases within the ARD) in SEQ. ID NO. 1 over the time course of the assay. Similar to SEQ. ID NO. 1, ARD also caused an increase in fluorescence over time in SEQ. ID NO. 2. Therefore, SEQ. ID NO. 2 can be utilized as a negative control/interferents sensor for the BoNT/A detection assay.

SEQ. ID NO. 1 Detects BoNT/A Activity in the Presence of Common PCR Inhibitors

To determine if common PCR inhibitors affect the ability of SEQ. ID NO. 1 to detect the activity of BoNT/A-LC in the presence of common PCR inhibitors, diesel exhaust (FIG. 17) and humic acid (FIG. 18) were tested. SEQ. ID NO. 1 (1 μM) was incubated with BoNT/A-LC (2.5 and 5 ng) in the presence of non-diluted diesel exhaust (30% assay volume) or humic acid (250 ng/mL) in a 96 well plate (100 μL per well; 30 mM Hepes pH 7.4, 0.2% Tween 20) and analyzed on the FilterMax® F5 fluorimeter at 37° C. for 60 minutes, with fluorescence readings taken at 1 minute intervals. As seen in FIGS. 17 and 18, while common PCR inhibitors slightly affect the overall fluorescence in the BoNT/A detection assay, small amounts of BoNT/A-LC were still capable of generating a large increase in fluorescence signal overtime. Therefore, SEQ. ID NO. 1 can detect BoNT/A-LC activity in the presence of common PCR inhibitors.

BoNT/A Assay Reducing Agent Optimization Using TCEP and DTT

Next, the assay was optimized to work with the full length BoNT/A (containing both heavy and light chains). Initially, the assay was optimized to work with 0.3 mM $ZnCl_2$ and the 2.5 mM DTT reducing agent. However, TCEP, a reducing agent more stable than DTT and that does not chelate zinc, was tested in the BoNT/A assay. SEQ. ID NO. 1 (1 μM) was used in a detection assay with BoNT/A-LC (5 ng) either with DTT (2.5 mM, with 0.3 mM $ZnCl_2$), TCEP (2.5 mM) or no reducing agent, in a 96 well plate (100 μL per well; 30 mM Hepes pH 7.4, 0.2% Tween 20). The reactions were incubated at 37° C. for 60 minutes in the FilterMax® F5 fluorimeter, with fluorescence readings taken at 1 minute intervals. As seen in FIG. 19, samples with 2.5 mM TCEP performed better than samples with DTT (and zinc), and even better than samples containing no reducing agent. Therefore, TCEP was chosen as the reducing agent used in the BoNT/A activity detection assay.

Detection of Full BoNT/A Holotoxin Complex in the BoNT/A Assay with TCEP

To determine the optimal TCEP concentration required for BoNT/A Holotoxin detection, SEQ. ID NO. 1 (1 μM) was used in a detection assay with BoNT/A Holotoxin (5 ng) either with or without TCEP (1.0 and 2.0 mM), in a 96 well plate (100 μL per well; 30 mM Hepes pH 7.4, 0.2% Tween 20). The reactions were incubated at 37° C. for 60 minutes in the FilterMax® F5 fluorimeter, with fluorescence readings taken at 1 minute intervals. As seen in FIG. 20, samples with 1.0 mM TCEP performed better than samples with 2.0 mM TCEP, noted by the greater increase in fluorescence over time. As expected, samples that did not contain TCEP were unable to detect BoNT/A Holotoxin. Therefore, 1.0 mM TCEP was chosen as the reducing agent concentration used in the BoNT/A activity detection assay.

BoNT/A Assay Development and Optimization in the RAZOR® EX Using SEQ. ID NO. 1 and 2

One embodiment of the present invention is an assay to detect biologically active BoNT/A on a qPCR platform. The previous buffer optimizations and designed fluorescence peptide substrates which were optimized on the FilterMax® F5 fluorimeter can be translated to perform on a qPCR platform. To test this, the RAZOR® EX qPCR protocol was optimized (based on information gathered from assays performed on the RAZOR® EX with SNAPtide®). The optimizations consisted of making an isothermal cycling protocol to be run at 37° C., adapting the read times to be performed at 1 minute intervals, and collecting PCR run data as raw data for subsequent graphing and algorithm processing. As seen in FIG. 21, SEQ. ID NO. 1 and SEQ. ID NO. 2 (both at 1 μM) were used in a detection assay with BoNT/A-LC (7.5 ng) in a 6×2 pouch (200 μL per well; 30 mM Hepes pH 7.4, 0.2% Tween 20, 1.0 mM TCEP). The reactions were incubated at 37° C. for 45 minutes in the RAZOR® EX, with fluorescence read at 1 minute intervals. While this assay was for a total of 45 minutes, such a strong positive signal was generated against a low background signal that a positive BoNT/A determination based on algorithmic determination and weighting (based on overall fluorescence increase and increase in fluorescence slope) could be made within approximately 10 minutes (10 cycles).

BoNT/A Assay Development and Optimization in the Genedrive® Using SEQ. ID NO. 1 at 42° C.

To further test the BoNT/A assay, we utilized the Genedrive® portable qPCR system. To test this assay, we first optimized the Genedrive® qPCR protocol making an isothermal cycling protocol to be run at 42° C. (standardized on this machine), adapting the read times to be performed at 1 second intervals, and collecting PCR run data as raw data for subsequent graphing and algorithm processing. As seen in FIG. 22, SEQ. ID NO. 1 (1 μM) was used in a detection assay with BoNT/A-LC (1.0 and 5.0 ng) in a 3×1 Genedrive® cassette (20 μL per well; 30 mM Hepes pH 7.4, 0.2% Tween 20, 1.0 mM TCEP). The reactions were incubated at 42° C. for 60 minutes in the Genedrive®, with fluorescence readings taken at 1 second intervals. While this assay was run for a total of 60 minutes, such a strong positive signal was generated against a background signal that a positive BoNT/A determination based on algorithmic determination and weighting (based on overall fluorescence increase and increase in fluorescence slope) could be made within approximately 15 minutes. Additionally, these results show that the BoNT/A assay can be run at 42° C., as well at 37° C.

BoNT/A Assay Limits of Detection Using SEQ. ID NO. 1

To determine the limit of detection of biologically active BoNT/A LC using SEQ. ID NO. 1, SEQ. ID NO. 1 (1 μM) was incubated with varying amounts of BoNT/A-LC (0.008, 0.04, and 0.2 ng) in a 96 well plate (100 μL per well; 30 mM Hepes pH 7.4, 0.2% Tween 20, 1.0 mM TCEP) and analyzed on the FilterMax® F5 fluorimeter at 37° C. for 60 minutes, with fluorescence readings taken at 1 minute intervals. As seen in FIG. 23, the limit of the detection for the SEQ. ID NO. 1 BoNT/A activity assay was at least 0.04 ng BoNT/A-LC over a 60 minute time period. Longer incubations may increase this limit of detection.

Development and Optimization of a Toxin Algorithm for the Detection of BoNT/A

The algorithm according to the present invention was developed to allow the presence or absence determination of biologically active toxin on a qPCR platform. The detection algorithm that is typically included in qPCR fluorescence detection instruments (e.g. Rotor-Gene® Q, RAZOR® EX, Genedrive®) is optimized to interpret fluorescence data from individual genetic samples that generate exponential increases in fluorescence when a critical threshold (CT) point is achieved. Genetic samples are "called positive" by a qPCR instrument's algorithm based on this exponential fluorescence increase (graphically displayed as a sigmoidal curve; cycle vs. fluorescence), which can be distinguished from negative samples that do not generate exponential fluorescence increases (graphically displayed as a flat straight line). Contrary to genetic samples, toxin samples generate non-exponential increases in fluorescence (graphically displayed as a straight line with a positive slope; time vs. fluorescence). Additionally, toxin samples require the comparison of the unknown samples (could be positive or negative) to a control sample (a negative sample) to determine a signal to noise ratio. Therefore, a qPCR instrument's genetic algorithm, which inherently lacks the capability to factor in a signal to noise ratio and is weighted to distinguish exponential data from non-exponential data, is not useful for data generated from toxin assays.

The first approach that was applied to the data from the initial SNAPtide experiments was to compare the fluorescence at the end of each cycle to a threshold value. The concept was that biologically active toxin was present in the sample if a specified threshold was exceeded; otherwise, toxin was absent from the sample. Observations of the results from this initial approach (data not shown) showed that this method was unreliable as background noise could exceed the threshold under certain conditions (e.g., interferents). These observations helped to illustrate the importance of using a negative control for determining the level of background fluorescence.

Development of the algorithm began by importing the raw data outputs into Microsoft Excel for 152 sample sets run on the FilterMax® F5 fluorimeter and 15 sample sets run on the RAZOR® EX. The purpose of this was to chart the data for comparison and performing investigative calculations to identify trends and conditions of significance. The following progression was applied to each of these 167 sample sets. First, the raw fluorescence values were graphed, as seen in FIG. 25, for both the assay and the negative control. This graph illustrated that the two lines diverged, but also experienced marked variability between consecutive cycles. Next, the average fluorescence of the negative control was graphed, as seen in FIG. 26, to smooth out the variability of the unprocessed data. The background/negative control data values were then subtracted from the assay data values and graphed, as seen in FIG. 26, for comparison. This illustrated that the background fluorescence could vary somewhat depending on which well or lane the sample was tested in because some of the subtractions resulted in a fluorescence value less than zero for the assay, which is not an actual possible condition.

The divergence of assay fluorescence values from the negative control fluorescence was identified as an important contributor to determining the presence of a biologically active toxin, but it was also identified that the rate at which these values diverged (or the slope of the curve) was also important. To study this, graphs of the slopes at each cycle, as seen in FIG. 27, and the change in the slope over time, as seen in FIG. 28, were created. These graphs showed that it could be difficult to compare the slope of the background fluorescence curve with the slope of the assay curve at each cycle with a good degree of accuracy. The cumulative slope, as seen in FIG. 29, and the deltas between cycles of the cumulative slope, as seen FIG. 30, were then graphed, which demonstrate that there is a higher variability in the first 10 cycles of a run. This finding lead to the conclusion that we needed an algorithm that could even out the high variability over time. Comparisons of the discrete and cumulative slopes for unprocessed values, as see in FIGS. 31 and 32, and background adjusted values, as seen in FIGS. 33 and 34, were graphed to reinforce the idea that the algorithm should be using an averaged slope value instead of the slope at a specified point in time.

Analysis of the standard deviations of fluorescence values for the assay, negative control, and the averages of these showed that there is a more noticeable increase over time for the assay than for the negative control, as seen in FIG. 35. This finding started on the path to using standard deviation as the preferred unit of measure for determining if biologically active toxin is present in a sample. Next, the standard deviations of the discrete sloped, as seen in FIG. 36, and cumulative sloped, as seen in FIG. 37, were compared. This confirmed findings from previous comparisons that cumulative slope is a better indicator of the presence of biologically active toxin and that standard deviation is an acceptable unit of measure to use for this determination. All of these findings were used as inputs to developing the toxin detection algorithm.

In order to implement the botulinum assay of the present invention in a legacy or conventional real-time PCR detector that is adapted strictly for real-time PCR routines and assays, the present invention also encompasses a detection algorithm to identify the presence of biologically active toxin that is instrument independent. The algorithm of the present invention is intended to be applied periodically at the end of each time cycle during an assay, and the output from the algorithm becomes more reliable as the number of completed cycles increases. The contributing factors to the algorithm are the fluorescence values as measured by the instrument of choice and the change in fluorescence over time. The algorithm requires a negative control assay sample to be run simultaneously on the same instrument, which provides a measure of the background fluorescence in the sample not resulting from peptide cleavage activity by a toxin (e.g., BoNT/A).

More specifically, the algorithm determines if the fluorescence and the change over time in fluorescence for the assay differ significantly enough from the negative control background fluorescence and the change in background fluorescence to indicate peptide cleavage activity. The magnitude of the delta from the background values is positively correlated to the likelihood of the presence of biologically active toxin. The larger the differences for each of the factors, the higher the likelihood that BoNT/A is present in the sample.

The algorithm relies on fluorescence values that have been obtained for all completed time cycles. First, the standard deviation and average fluorescence are calculated for the negative control fluorescence values. The average fluorescence is also calculated from the sample control values. Using these calculated values, the algorithm determines the number of positive standard deviations (up to 10) between the negative control average fluorescence and the sample average fluorescence. (A sample average fluorescence lower than the negative control average fluorescence is assigned a resulting value of 0 standard deviations.) The resulting number is then weighted by the fluorescence weight factor to obtain the fluorescence sub-score for that cycle. A fluorescence weight factor is used to assign the level of importance that fluorescence contributes to the determination of the presence or absence of a biologically active toxin. The fluorescence sub-scores are added together to achieve the overall fluorescence sub-score.

Next, the change in fluorescence (slope) between consecutive cycles is evaluated. The standard deviation and average slope are calculated for the negative control fluorescence values. The average slope is also calculated from the sample control values. Using these calculated values, the algorithm determines the number of positive standard deviations (up to 10) between the negative control average slope and the sample average slope. (A sample average slope lower than the negative control average slope is assigned a resulting value of 0 standard deviations.) The resulting number is then weighted by the slope weight factor to obtain the slope sub-score for that cycle. A slope weight factor is used to assign the level of importance that slope contributes to the determination of the presence or absence of a biologically active toxin. The slope sub-scores are added together to achieve the overall slope sub-score.

The overall fluorescence sub-score and the overall slope sub-score are then added together and then divided by the maximum possible points to arrive at the likelihood score. This score can then be compared to one or more thresholds to provide a ranking of the presence of biologically active toxin. For instance, comparing the score against a single threshold will indicate positive vs. negative. Similarly, comparing the score against three thresholds or ranges will provide low, medium, high indications of a positive presence of the biologically active toxin.

EXAMPLE 2

The mathematical formulas and variables for determining each of the steps of the algorithm may be seen in FIG. 24. FIGS. 25-37 are graphs of the results of the steps of the algorithm of the present invention as applied to the exemplary raw test data of Table 2 below:

TABLE 2

| Raw Test Data | | | | | | | |
|---|---|---|---|---|---|---|---|
| 0:00:00 | 1 | 17219782 | 16639028 | 16929405 | 16941250 | 16127615 | 16534432.5 |
| 0:01:03 | 2 | 16954224 | 16570812 | 16762518 | 16898200 | 16291588 | 16594894 |

TABLE 2-continued Raw Test Data

| | | | | | | | |
|---|---|---|---|---|---|---|---|
| 0:02:06 | 3 | 17348886 | 16617691 | 16983288.5 | 17064096 | 16192753 | 16628424.5 |
| 0:03:09 | 4 | 17037452 | 16571507 | 16804479.5 | 16868470 | 16139195 | 16503832.5 |
| 0:04:12 | 5 | 17063478 | 16493083 | 16778280.5 | 16974956 | 16113786 | 16544371 |
| 0:05:15 | 6 | 16995928 | 16555440 | 16775684 | 16897506 | 16102262 | 16499884 |
| 0:06:18 | 7 | 16997406 | 16522870 | 16760138 | 16928310 | 16102754 | 16515532 |
| 0:07:21 | 8 | 17049742 | 16419397 | 16734569.5 | 16958966 | 16182215 | 16570590.5 |
| 0:08:24 | 9 | 17187260 | 16568604 | 16877932 | 16991158 | 16241493 | 16616325.5 |
| 0:09:27 | 10 | 17127746 | 16612530 | 16870138 | 17091148 | 16158359 | 16624753.5 |
| 0:10:29 | 11 | 17489694 | 16721705 | 17105699.5 | 17135356 | 16393144 | 16764250 |
| 0:11:32 | 12 | 17073140 | 16455406 | 16764273 | 17003150 | 16292940 | 16648045 |
| 0:12:35 | 13 | 17162860 | 16651130 | 16906995 | 17032674 | 16263690 | 16648182 |
| 0:13:38 | 14 | 17180334 | 16635167 | 16907750.5 | 17168432 | 16399479 | 16783955.5 |
| 0:14:41 | 15 | 17290586 | 16598597 | 16944591.5 | 17113964 | 16396502 | 16755233 |
| 0:15:44 | 16 | 17302706 | 16724791 | 17013748.5 | 17235722 | 16379507 | 16807614.5 |
| 0:16:47 | 17 | 17419846 | 16856302 | 17138074 | 17346484 | 16612662 | 16979573 |
| 0:17:50 | 18 | 17548768 | 16974448 | 17261608 | 17374476 | 16559293 | 16966884.5 |
| 0:18:53 | 19 | 17431150 | 16769061 | 17100105.5 | 17402868 | 16559305 | 16981086.5 |
| 0:19:56 | 20 | 17525446 | 16787790 | 17156618 | 17441596 | 16634751 | 17038173.5 |
| 0:20:59 | 21 | 17443736 | 16832370 | 17138053 | 17433534 | 16665144 | 17049339 |
| 0:22:02 | 22 | 17502950 | 16827952 | 17165451 | 17464344 | 16838100 | 17151222 |
| 0:23:05 | 23 | 17767910 | 17002642 | 17385276 | 17661374 | 16788834 | 17225104 |
| 0:24:08 | 24 | 17409266 | 16875390 | 17142328 | 17625426 | 16799602 | 17212514 |
| 0:25:11 | 25 | 17439062 | 16791298 | 17115180 | 17603460 | 16859024 | 17231242 |
| 0:26:14 | 26 | 17844372 | 16958290 | 17401331 | 17690426 | 16814306 | 17252366 |
| 0:27:17 | 27 | 17522334 | 16931420 | 17226877 | 17606234 | 16768304 | 17187269 |
| 0:28:20 | 28 | 17472412 | 16915442 | 17193927 | 17705496 | 16960658 | 17333077 |
| 0:29:23 | 29 | 17535798 | 17028778 | 17282288 | 17857644 | 17060324 | 17458984 |
| 0:30:26 | 30 | 17630158 | 17067400 | 17348779 | 17948812 | 17170650 | 17559731 |
| 0:31:29 | 31 | 17606646 | 16984718 | 17295682 | 17762786 | 17053586 | 17408186 |
| 0:32:32 | 32 | 17582174 | 16880812 | 17231493 | 18037586 | 17240350 | 17638968 |
| 0:33:34 | 33 | 17613928 | 17060662 | 17337295 | 17886246 | 17218370 | 17552308 |
| 0:34:37 | 34 | 17564772 | 17119882 | 17342327 | 17999864 | 17198184 | 17599024 |
| 0:35:40 | 35 | 17985124 | 17108548 | 17546836 | 18146340 | 17307620 | 17726980 |
| 0:36:43 | 36 | 17647100 | 17003370 | 17325235 | 18020932 | 17235566 | 17628249 |
| 0:37:46 | 37 | 17621018 | 17046734 | 17333876 | 18041022 | 17375910 | 17708466 |
| 0:38:49 | 38 | 17636718 | 17009510 | 17323114 | 17949748 | 17263460 | 17606604 |
| 0:39:52 | 39 | 17625832 | 16817450 | 17221641 | 17960704 | 17244136 | 17602420 |
| 0:40:55 | 40 | 17970444 | 17141602 | 17556023 | 18258588 | 17547610 | 17903099 |
| 0:41:58 | 41 | 17670898 | 17016084 | 17343491 | 18172040 | 17581468 | 17876754 |
| 0:43:01 | 42 | 17707308 | 17035982 | 17371645 | 18183054 | 17457358 | 17820206 |
| 0:44:04 | 43 | 17683410 | 17089802 | 17386606 | 18330410 | 17610868 | 17970639 |
| 0:45:07 | 44 | 17754202 | 17058480 | 17406341 | 18275842 | 17577324 | 17926583 |
| 0:46:10 | 45 | 17781308 | 17112792 | 17447050 | 18463180 | 17673186 | 18068183 |
| 0:47:13 | 46 | 17724302 | 17110662 | 17417482 | 18385432 | 17806612 | 18096022 |
| 0:48:16 | 47 | 17716832 | 17185570 | 17451201 | 18513974 | 17789102 | 18151538 |
| 0:49:19 | 48 | 17733516 | 17043026 | 17388271 | 18561598 | 17705960 | 18133779 |
| 0:50:22 | 49 | 17684590 | 17028736 | 17356663 | 18436202 | 17776382 | 18106292 |
| 0:51:24 | 50 | 17610388 | 17012552 | 17311470 | 18454758 | 17701072 | 18077915 |
| 0:52:27 | 51 | 17635742 | 17042302 | 17339022 | 18607506 | 17856482 | 18231994 |
| 0:53:30 | 52 | 17937962 | 17134502 | 17536232 | 18486846 | 17739870 | 18113358 |
| 0:54:33 | 53 | 17711400 | 17081744 | 17396572 | 18525500 | 17660466 | 18092983 |
| 0:55:36 | 54 | 17746340 | 17135416 | 17440878 | 18654216 | 17912552 | 18283384 |
| 0:56:39 | 55 | 18025748 | 17261254 | 17643501 | 18837796 | 18026790 | 18432293 |
| 0:57:42 | 56 | 17837154 | 17217404 | 17527279 | 18908546 | 18053532 | 18481039 |
| 0:58:45 | 57 | 17759734 | 17116800 | 17438267 | 18795458 | 18018540 | 18406999 |
| 0:59:48 | 58 | 17751840 | 17179348 | 17465594 | 18852418 | 18077902 | 18465160 |
| 1:00:51 | 59 | 17834238 | 17192950 | 17513594 | 18839772 | 18060456 | 18450114 |
| 1:01:54 | 60 | 17781560 | 17167442 | 17474501 | 18879812 | 18142536 | 18511174 |
| 1:02:57 | 61 | 17897182 | 17219990 | 17558586 | 18978560 | 18162694 | 18570627 |

It should be recognized by those of skill in the art that the algorithm of the present invention may be programmed into or as part of the operating system of a device, such as a real-time PCR detection system, to enable the detection algorithm to be applied to a target sample. For example, the algorithm may physically incorporated into a PCR instrument will depend on the PCR instrument and vendor cooperation, and could be done by implementing the algorithm in code modules added to the instrument. Alternatively, the algorithm may be implemented on a laptop connected to the PCR instrument to analyze the data if it is unable to be incorporated directly into the PCR instrument

SEQUENCE LISTING

<160> NUMBER OF SEQ ID NOS: 6

<210> SEQ ID NO 1
<211> LENGTH: 57
<212> TYPE: PRT

```
<213> ORGANISM: Artificial Sequence
<220> FEATURE:
<223> OTHER INFORMATION: fluorescence resonance energy transfer peptide

<400> SEQUENCE: 1

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Ile Met Glu Lys Ala Asp Ser Asn Thr Arg Ile Asp Glu
        35                  40                  45

Ala Asn Gln Arg Ala Thr Lys Met Leu
    50                  55

<210> SEQ ID NO 2
<211> LENGTH: 57
<212> TYPE: PRT
<213> ORGANISM: Artificial Sequence
<220> FEATURE:
<223> OTHER INFORMATION: fluorescence resonance energy transfer peptide

<400> SEQUENCE: 2

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Ile Met Glu Lys Ala Asp Ser Asn Thr Arg Glu Asp Ile
        35                  40                  45

Gln Ala Thr Asn Arg Ala Lys Met Leu
    50                  55

<210> SEQ ID NO 3
<211> LENGTH: 57
<212> TYPE: PRT
<213> ORGANISM: Artificial Sequence
<220> FEATURE:
<223> OTHER INFORMATION: fluorescence resonance energy transfer peptide

<400> SEQUENCE: 3

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Ile Met Glu Lys Ala Asp Ser Asn Thr Arg Glu Asp Ile
        35                  40                  45

Gln Asn Ala Arg Thr Ala Lys Met Leu
    50                  55

<210> SEQ ID NO 4
<211> LENGTH: 57
<212> TYPE: PRT
<213> ORGANISM: Artificial Sequence
<220> FEATURE:
<223> OTHER INFORMATION: fluorescence resonance energy transfer peptide

<400> SEQUENCE: 4

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
            20                  25                  30

Ile Asp Arg Ile Met Glu Lys Ala Asp Ser Asn Thr Arg Glu Asp Ile
```

-continued

```
                  35                  40                  45
Gln Asn Ala Thr Ala Arg Lys Met Leu
        50                  55

<210> SEQ ID NO 5
<211> LENGTH: 57
<212> TYPE: PRT
<213> ORGANISM: Artificial Sequence
<220> FEATURE:
<223> OTHER INFORMATION: fluorescence resonance energy transfer peptide

<400> SEQUENCE: 5

Met Asp Glu Asn Leu Glu Gln Val Ser Gly Ile Ile Gly Asn Leu Arg
1               5                   10                  15

His Met Ala Leu Asp Met Gly Asn Glu Ile Asp Thr Gln Asn Arg Gln
                20                  25                  30

Ile Asp Arg Ile Met Glu Lys Ala Asp Ser Asn Thr Arg Glu Asp Ile
            35                  40                  45

Gln Asn Ala Thr Arg Ala Lys Met Leu
        50                  55

<210> SEQ ID NO 6
<211> LENGTH: 14
<212> TYPE: PRT
<213> ORGANISM: Artificial Sequence
<220> FEATURE:
<223> OTHER INFORMATION: fluorescence resonance energy transfer peptide

<400> SEQUENCE: 6

Thr Arg Ile Asp Glu Ala Asn Gln Arg Ala Thr Lys Met Leu
1               5                   10
```

What is claimed is:

1. A device for detecting the presence of biologically active botulinum toxin, comprising:
a chamber for receiving a test sample, said chamber including a peptide substrate comprising SEQ. ID NO. 1 that is labeled with a fluorophore and a quencher and has a cleavage site responsive to biologically active botulinum toxin positioned between said fluorophore and said quencher;
a detector for measuring the amount of fluorescence emitted from said sample and outputting a corresponding fluorescence reading positioned proximately to said chamber;
a microcontroller interconnected to said detector that is programmed to acquire said fluorescence reading and to determine whether any biologically active botulinum toxin is present in said sample based on said fluorescence reading.

2. The device of claim 1, wherein said chamber comprises a real-time PCR detector and said microcontroller is associated with said PCR detector and has been additionally programmed to acquire said fluorescence reading after a plurality of cycles and to determine whether any biologically active botulinum toxin is present in said sample based on the change in said fluorescence reading over a plurality of said cycles.

3. The device of claim 1, further comprising a negative control sample positioned in said chamber that has fluorescence that is separately detectable by said detector.

4. A device for detecting the presence of biologically active botulinum toxin, comprising:
a chamber for receiving a test sample, said chamber including a peptide substrate labeled with a fluorophore and a quencher and having a cleavage site responsive to biologically active botulinum toxin positioned between said fluorophore and said quencher;
a detector for measuring the amount of fluorescence emitted from said sample and outputting a corresponding fluorescence reading positioned proximately to said chamber;
a microcontroller interconnected to said detector that is programmed to acquire said fluorescence reading and to determine whether any biologically active botulinum toxin is present in said sample based on said fluorescence reading; and
a negative control sample positioned in said chamber that has fluorescence that is separately detectable by said detector, wherein said negative control sample is a peptide selected from the group consisting of SEQ. ID NO. 2, SEQ. ID NO. 3, SEQ. ID NO. 4, and SEQ. ID NO. 5.

5. The device of claim 3, wherein said microcontroller is programmed to determine whether biologically active botulinum toxin in present in said sample based on the change in magnitude of said fluorescence reading of said test sample over a plurality of said cycles relative to the change in magnitude of said fluorescence reading of said negative control sample over said plurality of said cycles.

6. The device of claim 5, wherein said microcontroller is further programmed to determine whether biologically active botulinum toxin in present in said sample based on an average change in slope of said fluorescence of said negative control sample over said plurality of said cycles and an average change in slope of said fluorescence of said test sample over said plurality of said cycles.

7. The device of claim 4, wherein said negative control sample is a peptide selected from the group consisting of SEQ. ID NO. 2, SEQ. ID NO. 3, SEQ. ID NO. 4, and SEQ. ID NO. 5.

* * * * *